US011612315B2

(12) United States Patent
Delong et al.

(10) Patent No.: US 11,612,315 B2
(45) Date of Patent: Mar. 28, 2023

(54) ALIGNMENT AND DIAGNOSTIC DEVICE AND METHODS FOR IMAGING AND SURGERY AT THE IRIDO-CORNEAL ANGLE OF THE EYE

(71) Applicant: ViaLase, Inc., Aliso Viejo, CA (US)

(72) Inventors: Scott A. Delong, Pagosa Springs, CO (US); Guy Holland, San Juan Capistrano, CA (US); Tibor Juhasz, San Clemente, CA (US); Wesley W. Lummis, Rancho Santa Margarita, CA (US); Eric R. Mikula, Aliso Viejo, CA (US); Attila Raksi, Mission Viejo, CA (US); Ferenc Raksi, Mission Viejo, CA (US); Manu Sharma, Ladera Ranch, CA (US); Hadi Srass, Yorba Linda, CA (US); Carlos G. Suarez, Tustin, CA (US); Joselito T. Tambo, Irvine, CA (US)

(73) Assignee: ViaLase, Inc., Aliso Viejo, CA (US)

( * ) Notice: Subject to any disclaimer, the term of this patent is extended or adjusted under 35 U.S.C. 154(b) by 318 days.

(21) Appl. No.: 16/844,655

(22) Filed: Apr. 9, 2020

(65) Prior Publication Data

US 2021/0315455 A1 Oct. 14, 2021

(51) Int. Cl.
*A61B 3/117* (2006.01)
*A61B 3/00* (2006.01)
(Continued)

(52) U.S. Cl.
CPC ............ *A61B 3/117* (2013.01); *A61B 3/0041* (2013.01); *A61B 3/102* (2013.01); *A61B 3/14* (2013.01);
(Continued)

(58) Field of Classification Search
CPC ....... A61B 3/117; A61B 3/0041; A61B 3/102; A61B 3/14; A61B 3/152; A61F 9/008;
(Continued)

(56) References Cited

U.S. PATENT DOCUMENTS

| 6,033,396 A | 3/2000 | Huang et al. |
|---|---|---|
| 6,251,103 B1 | 6/2001 | Berlin |

(Continued)

FOREIGN PATENT DOCUMENTS

| CN | 104382689 B | 9/2016 |
|---|---|---|
| DE | 4430720 A1 | 6/1995 |

(Continued)

OTHER PUBLICATIONS

PCT/US2021/025008. Int'l Search Report & Written Opinion. (dated Oct. 8, 2021).

(Continued)

*Primary Examiner* — Mohammed A Hasan
(74) *Attorney, Agent, or Firm* — Loza & Loza, LLP; David S. Sarisky

(57) ABSTRACT

A device for visualizing an irido-corneal angle of an eye through a window of a patient interface configured to be placed on the eye includes and optics structure and at least one imaging apparatus. The optics structure is configured to engage with the patient interface to provide a line of sight through the window in the direction of the irido-corneal angle, and to subsequently disengage from the patient interface. The imaging apparatus is associated with the optics structure and aligned with the line of sight to enable capturing an image of the eye including the irido-corneal angle.

33 Claims, 27 Drawing Sheets
(4 of 27 Drawing Sheet(s) Filed in Color)

(51) Int. Cl.
*A61B 3/10* (2006.01)
*A61B 3/14* (2006.01)
*A61F 9/008* (2006.01)

(52) U.S. Cl.
CPC .......... *A61F 9/008* (2013.01); *A61F 9/00825* (2013.01); *A61F 2009/00851* (2013.01); *A61F 2009/00868* (2013.01); *A61F 2009/00891* (2013.01)

(58) Field of Classification Search
CPC ........ A61F 9/00825; A61F 2009/00851; A61F 2009/00868; A61F 2009/00891
USPC ........................................................ 600/427
See application file for complete search history.

(56) References Cited

U.S. PATENT DOCUMENTS

| | | | |
|---|---|---|---|
| 6,482,199 B1 | 11/2002 | Neev | |
| 6,682,523 B2 | 1/2004 | Shadduck | |
| 6,989,007 B2 | 1/2006 | Shadduck | |
| 7,131,968 B2 | 11/2006 | Bendett et al. | |
| 7,192,412 B1 | 3/2007 | Zhou et al. | |
| 7,282,046 B2 | 10/2007 | Simon | |
| 7,351,241 B2 | 4/2008 | Bendett et al. | |
| 8,011,504 B1 | 9/2011 | Farberov | |
| 8,171,937 B2 | 5/2012 | Bendett et al. | |
| 8,230,866 B2 | 7/2012 | Hauger et al. | |
| 8,523,926 B2 | 9/2013 | Neev | |
| 8,540,659 B2 | 9/2013 | Berlin | |
| 8,568,393 B2 | 10/2013 | Palanker | |
| 8,679,089 B2 | 3/2014 | Berlin | |
| 8,687,866 B2 | 4/2014 | Marziliano et al. | |
| 8,845,624 B2 | 9/2014 | Raksi et al. | |
| 8,920,407 B2 | 12/2014 | Raksi et al. | |
| 9,033,963 B2 | 5/2015 | Vera et al. | |
| 9,044,303 B2 | 6/2015 | Kurtz et al. | |
| 9,259,153 B2 | 2/2016 | Goto | |
| 9,265,411 B2 | 2/2016 | Chen et al. | |
| 9,320,650 B2 | 4/2016 | Bendett et al. | |
| 9,441,946 B2 | 9/2016 | Massow et al. | |
| 9,456,925 B2 | 10/2016 | Kurtz et al. | |
| 9,498,295 B2 | 11/2016 | Palanker | |
| 9,517,006 B2 | 12/2016 | Izatt et al. | |
| 9,554,702 B2 | 1/2017 | Papac et al. | |
| 9,603,741 B2 | 3/2017 | Berlin | |
| 9,603,744 B2 | 3/2017 | Hailmann et al. | |
| 9,629,750 B2 | 4/2017 | Dambacher et al. | |
| 9,642,746 B2 | 5/2017 | Berlin | |
| 9,681,985 B2 | 6/2017 | Andersen et al. | |
| 9,724,238 B2 | 8/2017 | Heitel | |
| 9,750,640 B2 | 9/2017 | Palanker et al. | |
| 9,820,883 B2 | 11/2017 | Berlin | |
| 9,833,357 B2 | 12/2017 | Berlin | |
| 9,844,464 B2 | 12/2017 | Bendett et al. | |
| 9,936,868 B2 | 4/2018 | Izatt et al. | |
| 10,064,757 B2 | 9/2018 | Berlin | |
| 10,073,515 B2 | 9/2018 | Awdeh | |
| 10,159,600 B2 | 12/2018 | Horvath et al. | |
| 10,159,601 B2 | 12/2018 | Berlin | |
| 10,165,941 B2 | 1/2019 | Walsh et al. | |
| 10,179,066 B2 | 1/2019 | Badawi et al. | |
| 10,195,078 B2 | 2/2019 | Horvath et al. | |
| 10,195,079 B2 | 2/2019 | Horvath et al. | |
| 10,195,080 B2 | 2/2019 | Berlin | |
| 10,238,281 B2 | 3/2019 | Isogai et al. | |
| 10,238,541 B2 | 3/2019 | Yee et al. | |
| 10,292,868 B2 | 5/2019 | Chew et al. | |
| 10,335,314 B2 | 7/2019 | Berlin | |
| 10,360,683 B2 | 7/2019 | Iwase et al. | |
| 10,362,935 B2 | 7/2019 | Dastmalchi et al. | |
| 10,362,936 B2 | 7/2019 | Buckland et al. | |
| 10,363,169 B2 | 7/2019 | Belkin et al. | |
| 10,363,172 B2 | 7/2019 | Kawai et al. | |
| 10,383,689 B2 | 8/2019 | Berlin | |
| 10,390,883 B2 | 8/2019 | Deladurantaye et al. | |
| 10,398,306 B2 | 9/2019 | Liu | |
| 10,406,034 B2 | 9/2019 | Siegele | |
| 10,426,548 B2 | 10/2019 | Tearney et al. | |
| 10,456,030 B2 | 10/2019 | Buckland et al. | |
| 10,456,209 B2 | 10/2019 | Peyman | |
| 10,478,060 B2 | 11/2019 | Kubota | |
| 10,493,274 B2 | 12/2019 | Irazoqui et al. | |
| 10,499,809 B2 | 12/2019 | Kalina, Jr. et al. | |
| 10,500,094 B2 | 12/2019 | Buzawa et al. | |
| 10,517,760 B2 | 12/2019 | Berlin | |
| 10,524,822 B2 | 1/2020 | Aljuri et al. | |
| 10,537,476 B2 | 1/2020 | Ha et al. | |
| 10,542,883 B2 | 1/2020 | Gooi et al. | |
| 10,543,122 B2 | 1/2020 | Kahook | |
| 10,596,036 B2 | 3/2020 | Pinchuk | |
| 10,603,214 B2 | 3/2020 | Bigler et al. | |
| 10,603,216 B2 | 3/2020 | Kurtz et al. | |
| 10,653,557 B2 | 5/2020 | Rill et al. | |
| 10,674,906 B2 | 6/2020 | Kalina, Jr. et al. | |
| 10,687,978 B2 | 6/2020 | Berlin | |
| 10,702,416 B2 | 7/2020 | Belkin et al. | |
| 10,744,033 B2 | 8/2020 | Baerveldt et al. | |
| 10,744,034 B2 | 8/2020 | Homer | |
| 10,758,418 B2 | 9/2020 | Vold et al. | |
| 10,779,988 B2 | 9/2020 | Fu et al. | |
| 10,799,113 B2 | 10/2020 | Vadakke Matham et al. | |
| 10,821,023 B2 | 11/2020 | Raksi | |
| 10,821,024 B2 | 11/2020 | Raksi | |
| 10,888,461 B2 | 1/2021 | Orthaber et al. | |
| 2002/0013572 A1 | 1/2002 | Berlin | |
| 2004/0070761 A1 | 4/2004 | Horvath et al. | |
| 2006/0200113 A1 | 9/2006 | Haffner | |
| 2008/0058781 A1 | 3/2008 | Langeweyde et al. | |
| 2009/0012507 A1 | 1/2009 | Culbertson et al. | |
| 2009/0118718 A1 | 5/2009 | Raksi et al. | |
| 2009/0149840 A1 | 6/2009 | Kurtz | |
| 2009/0149841 A1 | 6/2009 | Kurtz | |
| 2009/0157062 A1* | 6/2009 | Hauger .................. A61B 3/102 606/5 |
| 2010/0130966 A1 | 5/2010 | Brownell | |
| 2011/0092965 A1 | 4/2011 | Slatkine et al. | |
| 2012/0257167 A1 | 10/2012 | Gille et al. | |
| 2012/0259321 A1 | 10/2012 | Vera et al. | |
| 2012/0283557 A1 | 11/2012 | Berlin | |
| 2012/0303007 A1 | 11/2012 | Loesel et al. | |
| 2013/0035672 A1 | 2/2013 | Raski | |
| 2013/0085484 A1 | 4/2013 | Van Valen et al. | |
| 2013/0103011 A1 | 4/2013 | Grant et al. | |
| 2013/0237972 A1 | 9/2013 | Raksi | |
| 2014/0142599 A1 | 5/2014 | Jeglorz et al. | |
| 2014/0216468 A1 | 8/2014 | Goldshleger et al. | |
| 2014/0236066 A1 | 8/2014 | Horvath et al. | |
| 2014/0288485 A1 | 9/2014 | Berlin | |
| 2014/0354951 A1 | 12/2014 | Izatt et al. | |
| 2015/0077528 A1 | 3/2015 | Awdeh | |
| 2015/0080783 A1 | 3/2015 | Berlin | |
| 2015/0157505 A1 | 6/2015 | Neev | |
| 2015/0297408 A1 | 10/2015 | Dolzan et al. | |
| 2015/0305939 A1 | 10/2015 | Vera et al. | |
| 2015/0305940 A1 | 10/2015 | Vera et al. | |
| 2015/0313759 A1 | 11/2015 | Vera et al. | |
| 2015/0335477 A1 | 11/2015 | Schuele et al. | |
| 2015/0359426 A1 | 12/2015 | Buckland et al. | |
| 2016/0095751 A1 | 4/2016 | Berlin | |
| 2016/0213512 A1 | 7/2016 | Palanker et al. | |
| 2016/0220110 A1 | 8/2016 | Vogler et al. | |
| 2017/0020732 A1 | 1/2017 | Berlin | |
| 2017/0027437 A1 | 2/2017 | Neal et al. | |
| 2017/0042736 A9 | 2/2017 | Berlin | |
| 2017/0119579 A9 | 5/2017 | Berlin | |
| 2017/0127938 A1 | 5/2017 | Izatt et al. | |
| 2017/0202708 A1 | 7/2017 | Berlin | |
| 2017/0326003 A1 | 11/2017 | Schuele et al. | |
| 2018/0028355 A1 | 2/2018 | Raksi | |
| 2018/0207029 A1* | 7/2018 | Herekar .............. A61F 9/00825 |
| 2018/0221205 A1 | 8/2018 | Berlin | |
| 2018/0235462 A1 | 8/2018 | Gooi et al. | |
| 2018/0360310 A1 | 12/2018 | Berlin | |

(56) References Cited

U.S. PATENT DOCUMENTS

| | | |
|---|---|---|
| 2018/0360655 A1 | 12/2018 | Berlin |
| 2019/0083313 A1 | 3/2019 | Berlin |
| 2019/0083314 A1 | 3/2019 | Berlin |
| 2019/0117459 A1 | 4/2019 | Berlin |
| 2019/0240070 A1 | 8/2019 | Schmid et al. |
| 2019/0357768 A1* | 11/2019 | Shareef .................. A61B 3/117 |
| 2020/0078216 A1 | 3/2020 | Raksi |
| 2020/0078217 A1 | 3/2020 | Raksi |
| 2020/0078218 A1* | 3/2020 | Holland .............. A61F 9/00825 |
| 2021/0022921 A1* | 1/2021 | Berlin .................... A61B 3/102 |
| 2021/0052416 A1 | 2/2021 | Herekar et al. |

FOREIGN PATENT DOCUMENTS

| | | |
|---|---|---|
| EP | 1080706 A1 | 3/2001 |
| EP | 1208792 A1 | 5/2002 |
| EP | 1017308 B1 | 6/2003 |
| EP | 2384727 A1 | 11/2011 |
| JP | S58187911 A | 11/1983 |
| JP | 2005508704 A | 4/2005 |
| JP | 2016504964 A | 2/2016 |
| WO | 2013188885 A1 | 12/2013 |
| WO | 2017031570 A1 | 3/2017 |
| WO | 2018049246 A1 | 3/2018 |
| WO | 2018073625 A1 | 4/2018 |
| WO | 2018218232 A1 | 11/2018 |
| WO | WO-2018218232 A1 * | 11/2018 ............. A61B 3/117 |
| WO | 2019060756 A1 | 3/2019 |
| WO | 2019173759 A1 | 9/2019 |

OTHER PUBLICATIONS

PCT/US2021/025008, Int'l Preliminary Examination Report (dated Apr. 4, 2022).

PCT/US2019/039033, Int'l Search Report & Written Opinion (dated Oct. 2, 2019).

PCT/US2019/039043, Int'l Search Report & Written Opinion (dated Oct. 10, 2019).

PCT/US2019/042553, Int'l Search Report & Written Opinion (dated Oct. 10, 2019).

PCT/US2019/042571, Int'l Search Report & Written Opinion (dated Oct. 15, 2019).

Brubaker, "Goldmann's equation and clinical measures of aqueous dynamics". Experimental Eye Research, vol. 78, Issue 3, pp. 633-637 (2004).

Grant, "Tonographic method for measuring the facility and rate of aqueous flow in human eyes". Arch. Ophthalmol. 44(2), pp. 204-214 (1950).

Hann et al. "Anatomic changes in schlemm's canal and collector channels in normal and primary open-angle glaucoma eyes using low and high perfusion pressures". Glaucoma, vol. 55:9 (Sep. 2014).

Johnstone, "The aqueous outflow system as a mechanical pump: evidence from examination of tissue and aqueous movement in human and non-human primates". J Glaucoma, vol. 13:5, pp. 421-438 (Oct. 2004).

Jones et al., "New methods of measuring the rate of aqueous flow in man with fluorescein". Experimental Eye Research, vol. 5:3, pp. 208-220 (Jul. 1966).

Junker et al. "Intraoperative optical coherence tomography and ab interno trabecular meshwork surgery with the trabectome." Clin Ophthalmol. 11: 1755-1760 (Sep. 28, 2017).

Kagemann et al. "Characterisation of Schlemm's canal cross-sectional area." Br J Ophthalmol 2014, 98 (Suppl. II) (Mar. 3, 2014).

Mcnabb et al. "Complete 360° circumferential gonioscopic optical coherence tomography imaging of the iridocorneal angle." Biomedical Optics Express vol. 6, Issue 4, pp. 1376-1391 (2015).

Rosenquist et al., "Ouflow resistance of enucleated human eyes at two different perfusion pressures and different extents of trabeculotomy". Current Eye Research, vol. 8:12, pp. 1233-1240 (1989).

Xin et al. "OCT study of mechanical properties associated with Trabecular meshwork and collector channel m,otion in human eyes." PLoS One. 2016; 11(9): e0162048. doi: 10.1371/journal.pone.0162048 (Sep. 6, 2016).

Xin et al. "Aqueous outflow regulation: optical coherence tomography implicates pressure-dependent tissue motion." Experimental Eye Research, vol. 158, pp. 171-186 (May 2017).

* cited by examiner

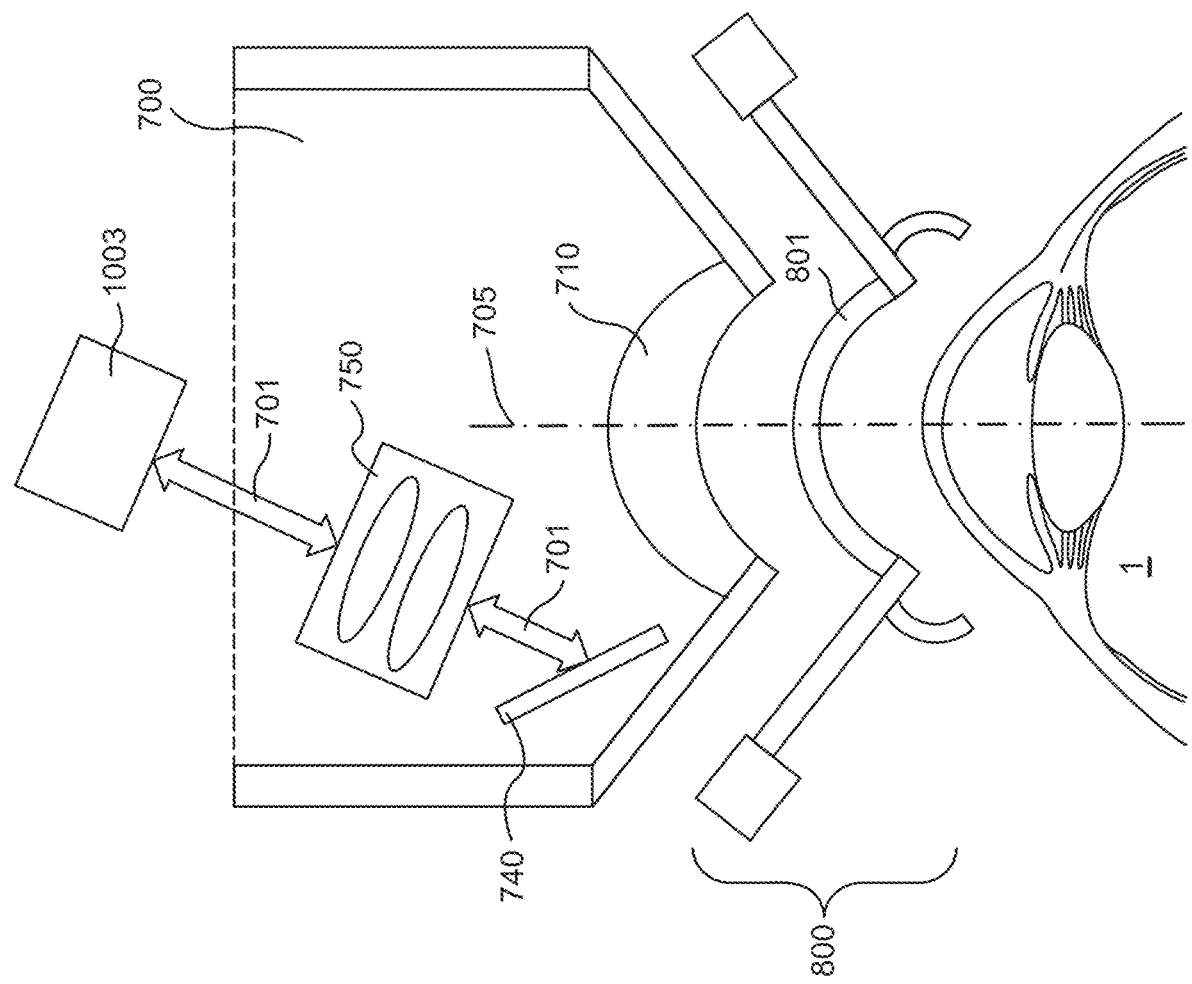

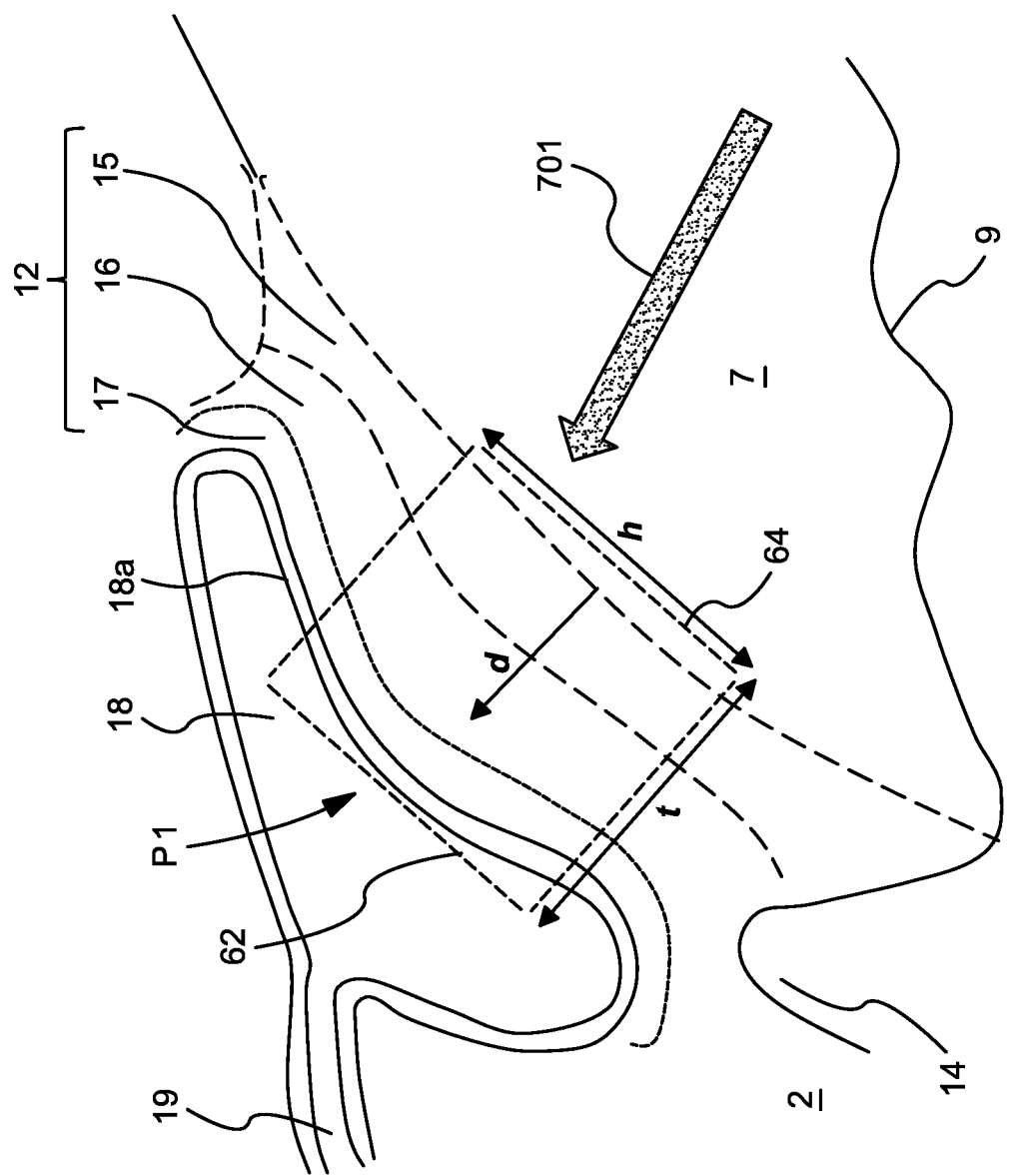
FIG. 11
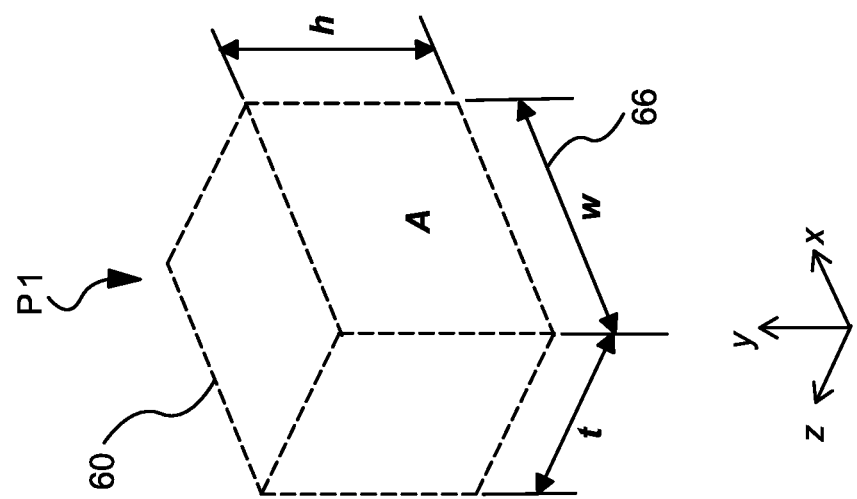

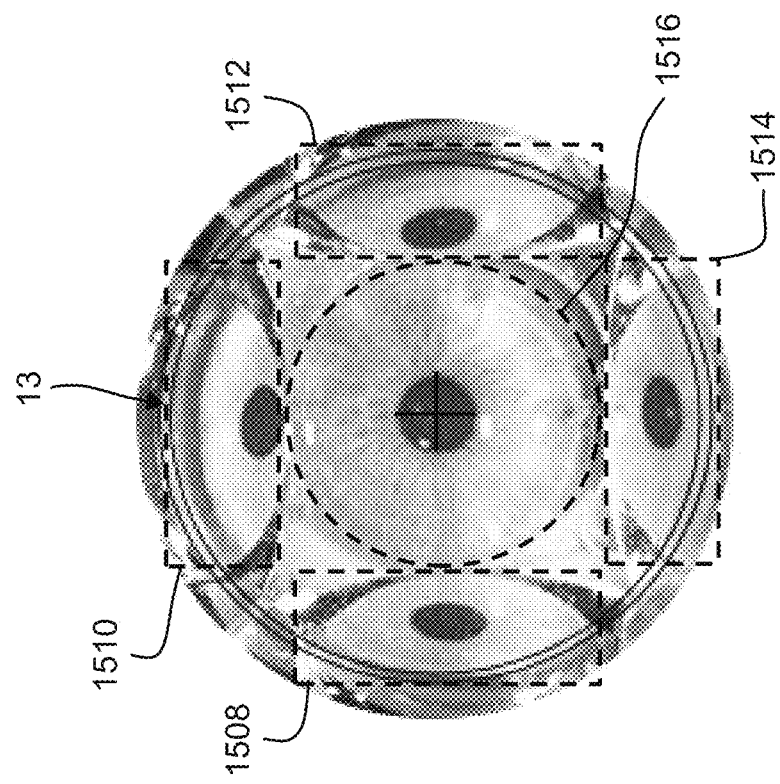
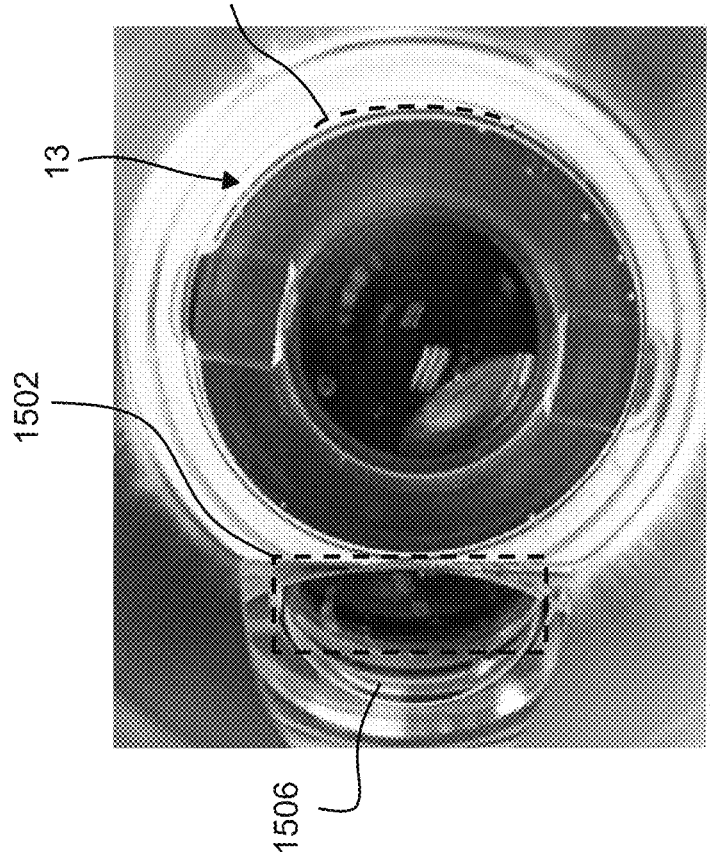
FIG. 15a
FIG. 15b

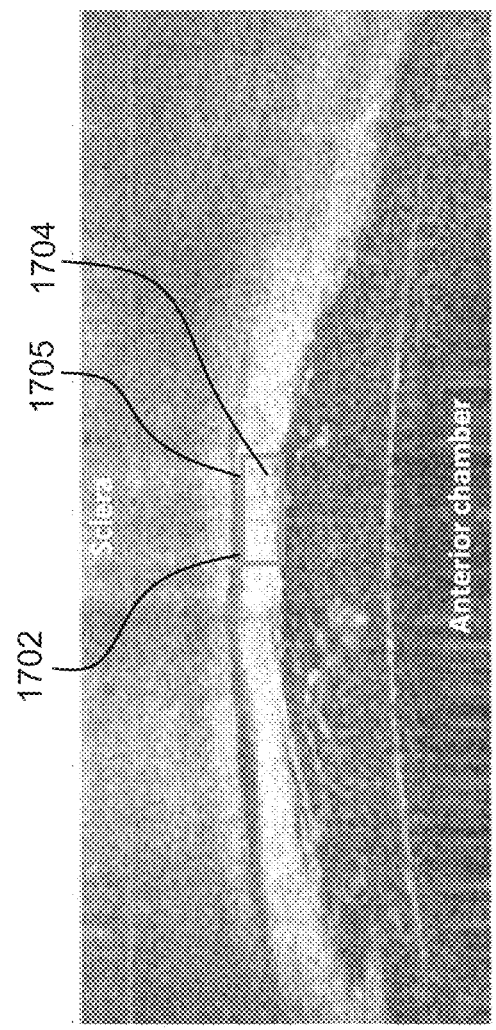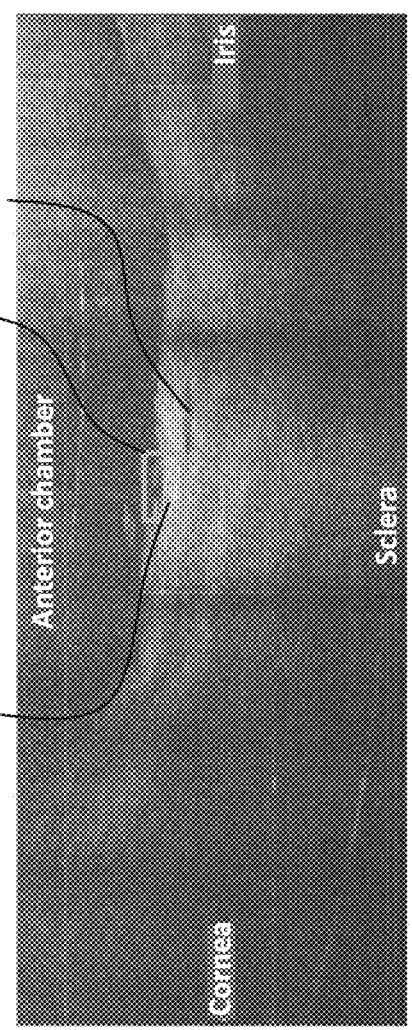
FIG. 17a
FIG. 17b

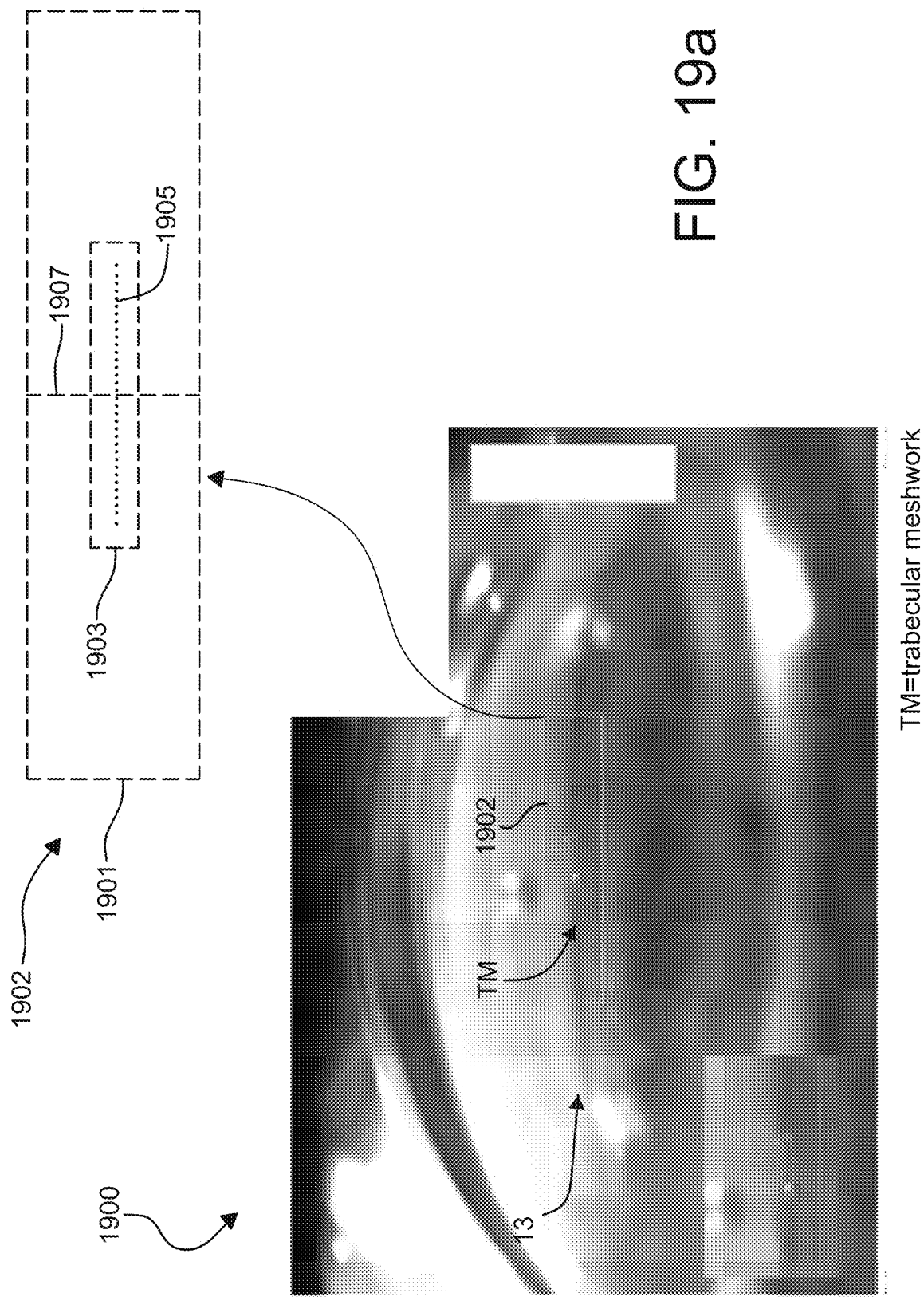

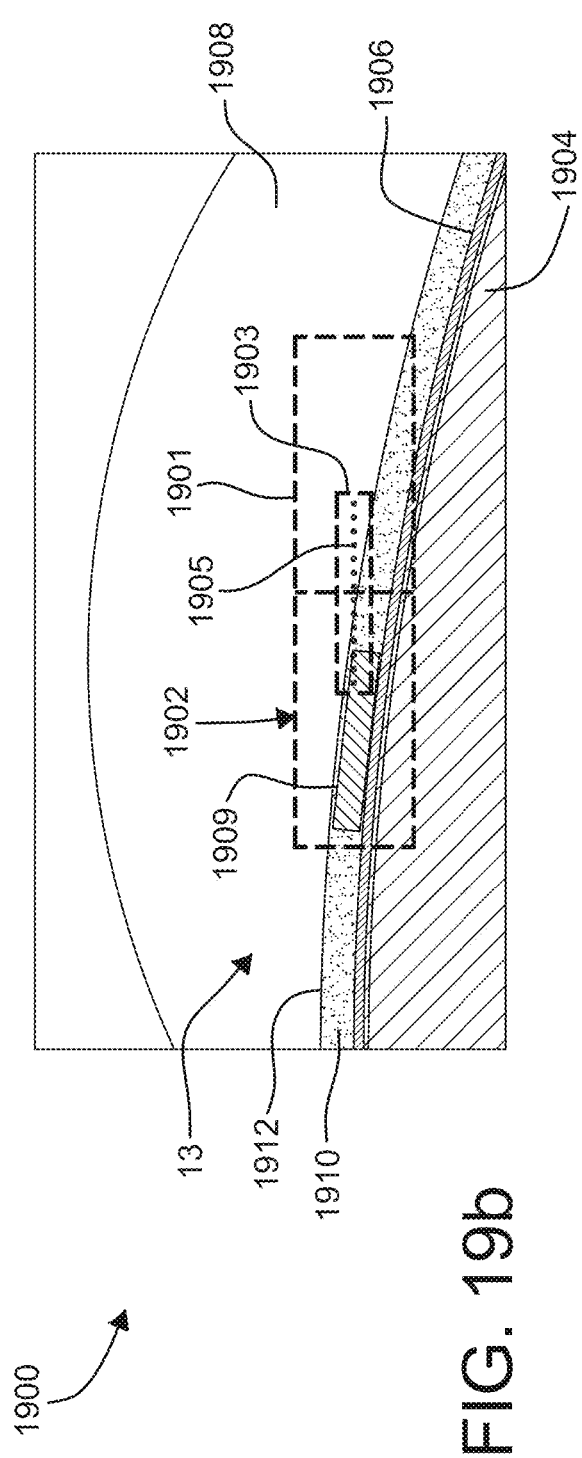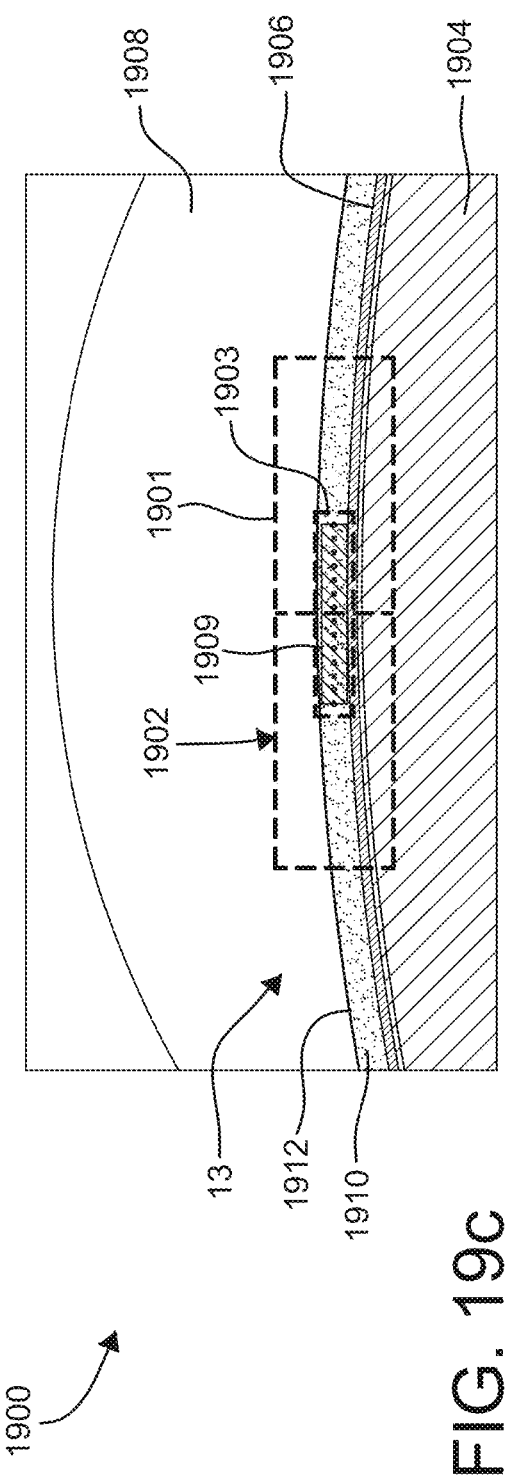
FIG. 19b
FIG. 19c

ALIGNMENT AND DIAGNOSTIC DEVICE AND METHODS FOR IMAGING AND SURGERY AT THE IRIDO-CORNEAL ANGLE OF THE EYE

TECHNICAL FIELD

The present disclosure relates generally to the field of medical devices and treatment of diseases in ophthalmology including glaucoma, and more particularly to an alignment and diagnostic device and methods for imaging and surgery at the irido-corneal angle of the eye.

BACKGROUND

Before describing the different types of glaucoma and current diagnosis and treatments options, a brief overview of the anatomy of the eye is provided.

Anatomy of the Eye

With reference to FIGS. 1-3, the outer tissue layer of the eye 1 includes a sclera 2 that provides the structure of the eye's shape. In front of the sclera 2 is a cornea 3 that is comprised of transparent layers of tissue that allow light to enter the interior of the eye. Inside the eye 1 is a crystalline lens 4 that is connected to the eye by fiber zonules 5, which are connected to the ciliary body 6. Between the crystalline lens 4 and the cornea 3 is an anterior chamber 7 that contains a flowing clear liquid called aqueous humor 8. Encircling the perimeter of the crystalline lens 4 is an iris 9 which forms a pupil around the approximate center of the crystalline lens. A posterior chamber 23 is an annular volume behind the iris 9 and bounded by the ciliary body 6, fiber zonules 5, and the crystalline lens 4. The vitreous humor 10 is located between the crystalline lens 4 and the retina 11. Light entering the eye is optically focused through the cornea 3 and crystalline lens.

With reference to FIG. 2, the corneoscleral junction of the eye is the portion of the anterior chamber 7 at the intersection of the iris 9, the sclera 2, and the cornea 3. The anatomy of the eye 1 at the corneoscleral junction includes a trabecular meshwork 12. The trabecular meshwork 12 is a fibrous network of tissue that encircles the iris 9 within the eye 1. In simplified, general terms the tissues of the corneoscleral junction are arranged as follows: the iris 9 meets the ciliary body 6, the ciliary body meets with the underside of the scleral spur 14, the top of the scleral spur serves as an attachment point for the bottom of the trabecular meshwork 12. The ciliary body is present mainly in the posterior chamber, but also extends into the very corner of the anterior chamber 7. The network of tissue layers that make up the trabecular meshwork 12 are porous and thus present a pathway for the egress of aqueous humor 8 flowing from the anterior chamber 7. This pathway may be referred to herein as an aqueous humor outflow pathway, an aqueous outflow pathway, or simply an outflow pathway.

Referring to FIG. 3, the pathway formed by the pores in the trabecular meshwork 12 connect to a set of thin porous tissue layers called the uveal 15, the corneoscleral meshwork 16, and the juxtacanalicular tissue 17. The juxtacanalicular tissue 17, in turn, abuts a structure called Schlemm's canal 18. The Schlemm's canal 18 carries a mixture of aqueous humor 8 and blood from the surrounding tissue to drain into the venous system though a system of collector channels 19. As shown in FIG. 2, the vascular layer of the eye, referred to as the choroid 20, is next to the sclera 2. A space, called the suprachoroidal space 21, may be present between the choroid 20 and the sclera 2. The general region near the periphery of the wedge between the cornea 3 and the iris 9, running circumferentially is called the irido-corneal angle 13. The irido-corneal angle 13 may also be referred to as the corneal angle of the eye or simply the angle of the eye. The ocular tissues illustrated in FIG. 3 are all considered to be within the irido-corneal angle 13.

With reference to FIG. 4, two possible outflow pathways for the movement of aqueous humor 8 include a trabecular outflow pathway 40 and a uveoscleral outflow pathway 42. Aqueous humor 8, which is produced by the ciliary body 6, flows from the posterior chamber 23 through the pupil into the anterior chamber 7, and then exits the eye through one or more of the two different outflow pathways 40, 42. Approximately 90% of the aqueous humor 8 leaves via the trabecular outflow pathway 40 by passing through the trabecular meshwork 12, into the Schlemm's canal 18 and through one or more plexus of collector channels 19 before draining through a drain path 41 into the venous system. Any remaining aqueous humor 8 leaves primarily through the uveoscleral outflow pathway 42. The uveoscleral outflow pathway 42 passes through the ciliary body 6 face and iris root into the suprachoroidal space 21 (shown in FIG. 2). Aqueous humor 8 drains from the suprachoroidal space 21, from which it can be drained through the sclera 2.

The intra-ocular pressure of the eye depends on the aqueous humor 8 outflow through the trabecular outflow pathway 40 and the resistance to outflow of aqueous humor through the trabecular outflow pathway. The intra-ocular pressure of the eye is largely independent of the aqueous humor 8 outflow through the uveoscleral outflow pathway 42. Resistance to the outflow of aqueous humor 8 through the trabecular outflow pathway 40 may lead to elevated intra-ocular pressure of the eye, which is a widely recognized risk factor for glaucoma. Resistance through the trabecular outflow pathway 40 may increase due a collapsed or malfunctioning Schlemm's canal 18 and trabecular meshwork 12.

Referring to FIG. 5, as an optical system, the eye 1 is represented by an optical model described by idealized centered and rotationally symmetrical surfaces, entrance and exit pupils, and six cardinal points: object and image space focal points, first and second principal planes, and first and second nodal points. Angular directions relative to the human eye are often defined with respect to an optical axis 24, a visual axis 26, a pupillary axis 28 and a line of sight 29 of the eye. The optical axis 24 is the symmetry axis, the line connecting the vertices of the idealized surfaces of the eye. The visual axis 26 connects the foveal center 22 with the first and second nodal points to the object. The line of sight 29 connects the fovea through the exit and entrance pupils to the object. The pupillary axis 28 is normal to the anterior surface of the cornea 3 and directed to the center of the entrance pupil. These axes of the eye differ from one another only by a few degrees and fall within a range of what is generally referred to as the direction of view.

Glaucoma

Glaucoma is a group of diseases that can harm the optic nerve and cause vision loss or blindness. It is the leading cause of irreversible blindness. Approximately 80 million people are estimated to have glaucoma worldwide and of these, approximately 6.7 million are bilaterally blind. More than 2.7 million Americans over age 40 have glaucoma. Symptoms start with loss of peripheral vision and can progress to blindness.

There are two forms of glaucoma, one is referred to as closed-angle glaucoma, the other as open-angled glaucoma. With reference to FIGS. 1-4, in closed-angle glaucoma, the iris 9 in a collapsed anterior chamber 7 may obstruct and close off the flow of aqueous humor 8. In open-angle glaucoma, which is the more common form of glaucoma, the permeability of ocular tissue may be affected by irregularities in the juxtacanalicular tissue 17 and inner wall of Schlemm's canal 18a, blockage of tissue in the irido-corneal angle 13 along the trabecular outflow pathway 40.

As previously stated, elevated intra-ocular pressure (IOP) of the eye, which damages the optic nerve, is a widely recognized risk factor for glaucoma. However, not every person with increased eye pressure will develop glaucoma, and glaucoma can develop without increased eye pressure. Nonetheless, it is desirable to reduce elevated IOP of the eye to reduce the risk of glaucoma.

Methods of diagnosing conditions of the eye of a patient with glaucoma include visual acuity tests and visual field tests, dilated eye exams, tonometry, i.e. measuring the intra-ocular pressure of the eye, and pachymetry, i.e. measuring the thickness of the cornea. Deterioration of vision starts with the narrowing of the visual field and progresses to total blindness. Imaging methods include slit lamp examination, observation of the irido-corneal angle with a gonioscopic lens and optical coherence tomography (OCT) imaging of the anterior chamber and the retina Once diagnosed, some clinically proven treatments are available to control or lower the intra-ocular pressure of the eye to slow or stop the progress of glaucoma. The most common treatments include: 1) medications, such as eye drops or pills, 2) laser surgery, and 3) traditional surgery. Treatment usually begins with medication. However, the efficacy of medication is often hindered by patient non-compliance. When medication does not work for a patient, laser surgery is typically the next treatment to be tried. Traditional surgery is invasive, more high risk than medication and laser surgery, and has a limited time window of effectiveness. Traditional surgery is thus usually reserved as a last option for patients whose eye pressure cannot be controlled with medication or laser surgery.

Laser Surgery

With reference to FIG. 2, laser surgery for glaucoma targets the trabecular meshwork 12 to decrease aqueous humor 8 flow resistance. Common laser treatments include Argon Laser Trabeculoplasty (ALT), Selective Laser Trabeculoplasty (SLT) and Excimer Laser Trabeculostomy (ELT).

ALT was the first laser trabeculoplasty procedure. During the procedure, an argon laser of 514 nm wavelength is applied to the trabecular meshwork 12 around 180 degrees of the circumference of the irido-corneal angle 13. The argon laser induces a thermal interaction with the ocular tissue that produces openings in the trabecular meshwork 12. ALT, however, causes scarring of the ocular tissue, followed by inflammatory responses and tissue healing that may ultimately close the opening through the trabecular meshwork 12 formed by the ALT treatment, thus reducing the efficacy of the treatment. Furthermore, because of this scarring, ALT therapy is typically not repeatable.

SLT is designed to lower the scarring effect by selectively targeting pigments in the trabecular meshwork 12 and reducing the amount of heat delivered to surrounding ocular tissue. During the procedure, a solid-state laser of 532 nm wavelength is applied to the trabecular meshwork 12 between 180 to 360 degrees around the circumference of the irido-corneal angle 13 to remove the pigmented cells lining the trabeculae which comprise the trabecular meshwork. The collagen ultrastructure of the trabecular meshwork is preserved during SLT. SLT treatment can be repeated, but subsequent treatments have lower effects on IOP reduction.

ELT uses a 308 nm wavelength ultraviolet (UV) excimer laser and non-thermal interaction with ocular tissue to treat the trabecular meshwork 12 and inner wall of Schlemm's canal in a manner that does not invoke a healing response. Therefore, the IOP lowering effect lasts longer. However, because the UV light of the laser cannot penetrate deep into the eye, the laser light is delivered to the trabecular meshwork 12 via an optical fiber inserted into the eye 1 through an opening and the fiber is brought into contact with the trabecular meshwork. The procedure is highly invasive and is generally practiced simultaneously with cataract procedures when the eye is already surgically open. Like ALT and SLT, ELT also lacks control over the amount of IOP reduction.

In these laser treatments, and other ophthalmic surgeries involving a laser, it is necessary to stabilize and fix the position of the eye relative to an optical delivery system through which the laser is output. This is particularly needed wherever highly precise incisions are created in the eye. In these treatments, a patient interface is first docked onto the eye. Suction is applied to a suction ring around the patient interface to fix the patient interface onto the eye. The optical delivery system is then locked into the patient interface. In this manner, the patient's eye and the laser output from the optical delivery system is aligned.

For glaucoma surgery the task of accurately positioning the patient interface is complicated by the fact that the laser treatment involves ocular tissue in the irido-corneal angle of the eye. Ophthalmic surgical instruments that access the irido-corneal angle of the eye have a limited surgical range in three-dimensional space where the specifications of the laser, imaging capability of the instrument and focusability of the laser are satisfied. Thus, proper alignment between the eye and optical delivery system is critical. Without such alignment, the intended surgical location on the eye may fall outside the field of view or the surgical range of the optical delivery system. In that case undesired repeated undocking and realignment of the eye is necessary.

SUMMARY

The present disclosure relates to a device for visualizing an irido-corneal angle of an eye through a window of a patient interface configured to be placed on the eye. The device includes an optics structure and at least one imaging apparatus. The optics structure is configured to engage with the patient interface to provide a line of sight through the window in a direction of the irido-corneal angle, and to subsequently disengage from the patient interface. The at least one imaging apparatus is associated with the optics structure and aligned with the line of sight to enable capturing an image of the eye including the irido-corneal angle.

The optics structure may be configured to provide the line of sight in the direction of the irido-corneal angle around at least a portion of a circumferential extent of the irido-corneal angle. The optics structure may be configured to provide the line of sight in the direction of the irido-corneal angle around an entire circumferential extent of the irido-corneal angle. The optics structure may be configured to rotate relative to the patient interface to enable a capturing of images at various angular positions around a circumferential extent of the irido-corneal angle.

The at least one imaging apparatus is configured to couple to the optics structure and the optics structure is configured to rotate relative to the patient interface together with the at least one imaging apparatus. The device may further include a locking mechanism associated with the optics structure.

The locking mechanism is configured to enable fixation of the optics structure relative to the patient interface at various angular positions around a circumferential extent of the irido-corneal angle.

The imaging apparatus may be a camera. The imaging apparatus may include one or more optical coherence tomography (OCT) components configured to couple with an OCT apparatus remote from the device. The imaging apparatus may include a dual aiming beam apparatus configured to transmit a first beam of light and a second beam light in the direction of the line of sight into the irido-corneal angle. The imaging apparatus may include a first fiber optic cable having an output aligned in the direction of the line of sight and a second fiber optic cable having an output aligned in the direction of the line of sight, wherein the first and second fiber optic cables are configured to couple to a dual aiming beam apparatus remote from the device so that the first fiber optic cable receives a first beam of light and the second fiber optic cable receives a second beam light. The imaging apparatus may be a second harmonic light detector aligned with the line of sight and configured to determine a location of a focus of a laser beam based on changes in an intensity of a spot of second harmonic light generated by an encounter between the focus and tissue. The device may further include an interface configured to couple to a laser source and to transmit a laser beam output by the laser source in the direction of the line of sight.

The present disclosure also relates to a method of aligning an eye for laser treatment of a target volume of ocular tissue in an irido-corneal angle by a laser surgical instrument having a surgical range. The method includes presenting an image of the eye on a display, wherein: the image is captured by an alignment and diagnostic device that is engaged with a patient interface to provide a line of sight in a direction of the irido-corneal angle, the display includes a surgical area overlay corresponding to the surgical range of the laser surgical instrument, and the alignment and diagnostic device is independent of the laser surgical instrument and is configured to engage with and subsequently disengage from the patient interface. The method also includes updating the display of the image during a movement of the patient interface and the alignment and diagnostic device relative to the eye, and immobilizing the patient interface relative to the eye when the display indicates that the target volume of ocular tissue is within the surgical area overlay.

The surgical area overlay may include a coarse surgical area overlay and a fine surgical area overlay located within the coarse surgical area overlay. The surgical area overlay may further include a circumference scanning mark, which indicates a length and an orientation of a circumferential optical coherence tomography (OCT) scan of an OCT imaging apparatus associated with the laser surgical instrument. The surgical area overlay may further include a transverse scanning mark that indicates a length and an orientation of a transverse optical coherence tomography (OCT) scan of an OCT imaging apparatus associated with the laser surgical instrument.

The method may further include, subsequent to immobilizing the patient interface relative to the eye, recording a circumferential angular position of the target volume of ocular tissue from a rotational registration of the alignment and diagnostic device; and removing the alignment and diagnostic device from the patient interface. The method may further include, subsequent to removing the alignment and diagnostic device from the patient interface: coupling the laser surgical instrument to the patient interface; setting a circumferential angular position of the laser surgical instrument to the circumferential angular position recorded for the alignment and diagnostic device; and focusing light from a laser at a spot in the target volume of ocular tissue; and applying optical energy at the spot in the target volume of ocular tissue. The method may further include, prior to focusing light from the laser at a spot in the target volume of ocular tissue: presenting an image of the eye on a display, wherein, the image is captured by a visual microscope optically coupled to the patient interface, and the display includes a surgical area overlay corresponding to the surgical range of the laser surgical instrument.

The method may further include prior to immobilizing the patient interface relative to the eye, determining if a depth fiducial of the target volume of ocular tissue is within a depth range of the laser surgical instrument. The determining may be based on a relative location of spots of light output by a dual aiming beam apparatus and a surface of the target volume of ocular tissue. The determining may be based on an interaction of second harmonic light and one or more anatomical landmarks of the target volume of ocular tissue.

It is understood that other aspects of apparatuses and methods will become apparent to those skilled in the art from the following detailed description, wherein various aspects of apparatuses and methods are shown and described by way of illustration. As will be realized, these aspects may be implemented in other and different forms and its several details are capable of modification in various other respects. Accordingly, the drawings and detailed description are to be regarded as illustrative in nature and not as restrictive.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

Various aspects of systems, apparatuses, and methods will now be presented in the detailed description by way of example, and not by way of limitation, with reference to the accompanying drawings, wherein:

FIGS. 9a and 9b are schematic illustrations of the focusing objective of the integrated surgical system of FIG. 7 coupled to (FIG. 9a) and decoupled from (FIG. 9b) the patient interface of the integrated surgical system of FIG. 7.

FIG. 11 is a two-dimensional schematic illustration of anatomical structures in the irido-corneal angle and a laser treatment pattern to be applied by the integrated surgical system of FIG. 7 to affect a surgical volume of ocular tissue between the Schlemm's canal and the anterior chamber as shown in FIG. 10.

FIG. 15a is an image of a portion of an irido-corneal angle of an eye captured by an alignment and diagnostic device having a single facet mirror.

FIG. 15b is image of portions of an irido-corneal angle captured by an alignment and diagnostic device having four facet mirrors.

FIGS. 17a and 17b images of a portion of an irido-corneal angle of an eye captured by an OCT apparatus in conjunction with an OCT component of an alignment and diagnostic device.

FIG. 19a is the image of FIG. 16 as it would appear on a display of an alignment and diagnostic device, with a surgical area overlay to assist in aligning the device relative to a target surgical location of the irido-corneal angle.

FIGS. 19b and 19c are schematic representations of an image of an irido-corneal angle of an eye captured by a camera of an alignment and diagnostic device with a surgical area overlay.

DETAILED DESCRIPTION

Disclosed herein is an alignment and diagnostic device and methods for imaging and surgery at the irido-corneal angle of the eye. The alignment and diagnostic device is a portable, handheld device that removably couples with a patient interface placed on the eye. The device enables visualization of the irido-corneal angle of the eye. Such visualization may be provided, for example, by a camera included in the device, or an optical coherence tomography (OCT) imaging component included in the device that couples to an OCT imaging apparatus. Movement of the device and patient interface relative to the eye during visualization enable an alignment of the patient interface on the eye that places a target surgical location in the irido-corneal angle in the surgical range of an integrated surgical system. Upon placement of the target surgical location in the surgical range, the patient interface is secured to the eye, the alignment and diagnostic device is removed from the eye, and the integrated surgical system is coupled to the patient interface for delivery of laser treatment to the target surgical location.

The integrated surgical system coupled to the patient interface is configured to reduce intraocular pressure in an eye having a cornea, an anterior chamber, and an irido-corneal angle comprising an aqueous humor outflow pathway formed of a trabecular meshwork, a Schlemm's canal, and one or more collector channels branching from the Schlemm's canal. The integrated surgical system also includes a first optical subsystem and a second optical subsystem. The first optical subsystem includes a window configured to be coupled to the cornea and an exit lens configured to be coupled to the window. The second optical subsystem includes an optical coherence tomography (OCT) imaging apparatus configured to output an OCT beam, a laser source configured to output a laser beam, and a plurality of components, e.g., lenses and mirrors, configured to condition, combine, or direct the OCT beam and the laser beam toward the first optical subsystem.

The integrated surgical system also includes a control system coupled to the OCT imaging apparatus, the laser source, and the second optical subsystem. The controller is configured to instruct the OCT imaging apparatus to output an OCT beam and the laser source to output a laser beam, for delivery through the cornea, and the anterior chamber into the irido-corneal angle. In one configuration, the control system controls the second optical subsystem, so the OCT beam and the laser beam are directed into the first optical subsystem along a second optical axis that is offset from the first optical axis and that extends into the irido-corneal angle along an angled beam path 30.

Figure 2:
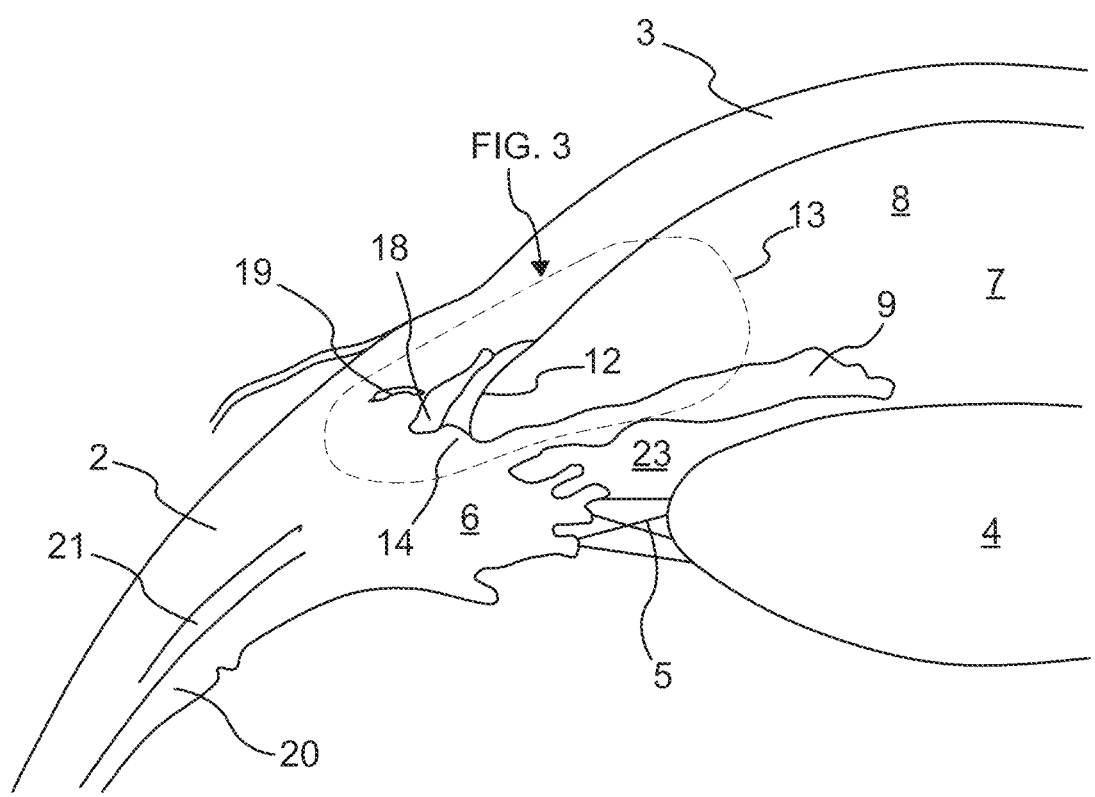
FIG. 2 is a sectional schematic illustration of the irido-corneal angle of the eye of FIG. 1.
Figure 3:
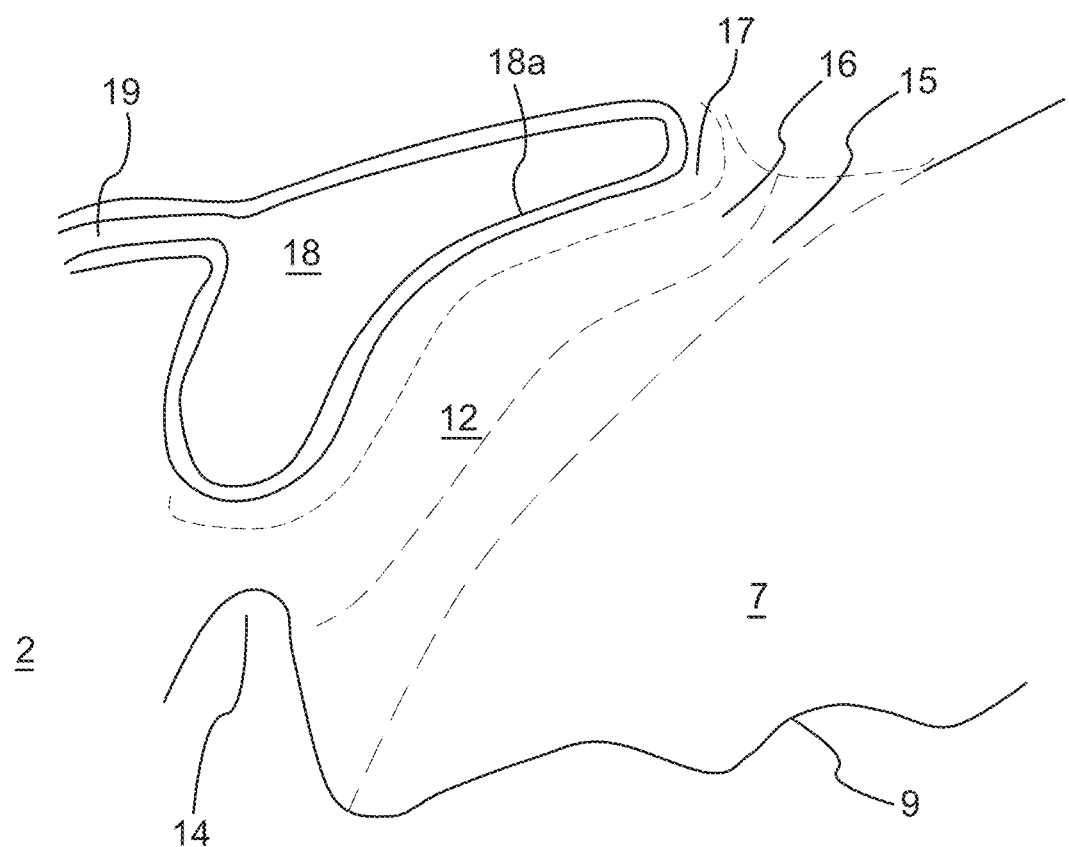
FIG. 3 is a sectional schematic illustration detailing anatomical structures in the irido-corneal angle of FIG. 2, including the trabecular meshwork, Schlemm's canal, and one or more collector channels branching from the Schlemm's canal.
Figure 4:
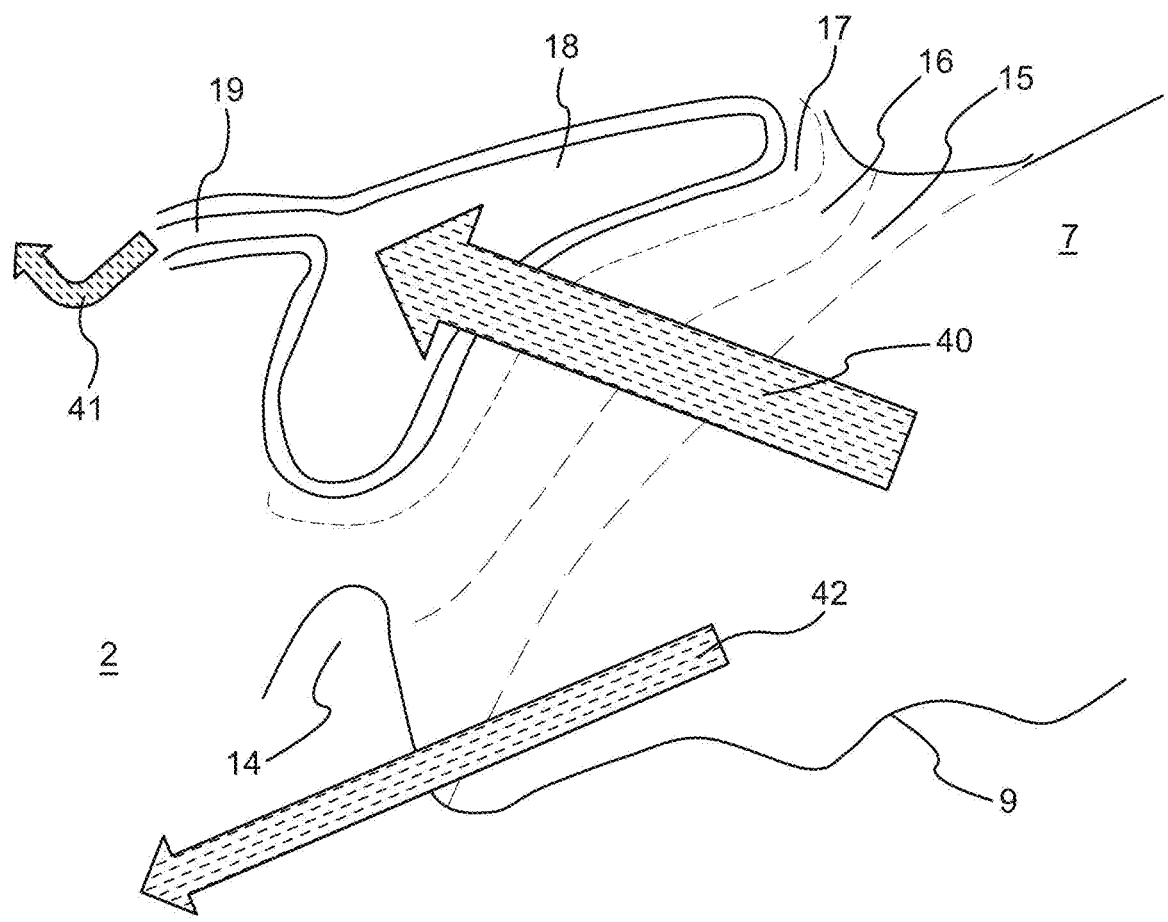
FIG. 4 is a sectional schematic illustration of various outflow pathways for aqueous humor through the trabecular meshwork, Schlemm's canal, and collector channels of FIG. 3.
Figure 5:
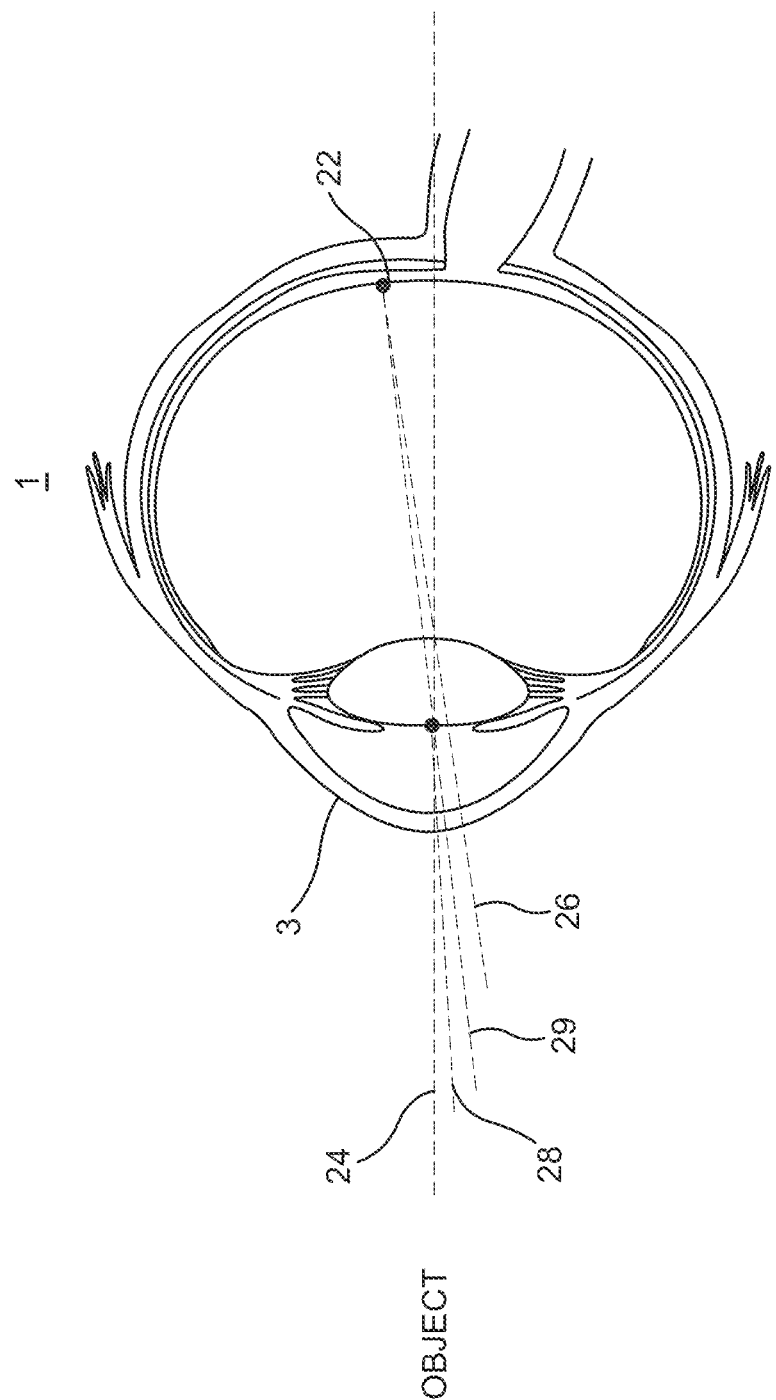
FIG. 5 is a sectional schematic illustration of a human eye showing various axes associated with the eye.

Directing each of an OCT beam and a laser beam along the same second optical axis into the irido-corneal angle of the eye is beneficial in that it enables direct application of the result of the evaluation of the condition into the treatment plan and surgery with precision in one clinical setting. Furthermore, combining OCT imaging and laser treatment allows targeting the ocular tissue with precision not available with any existing surgical systems and methods. Surgical precision afforded by the integrated surgical system allows for the affecting of only the targeted tissue of microscopic size and leaves the surrounding tissue intact. The microscopic size scale of the affected ocular tissue to be treated in the irido-corneal angle of the eye ranges from a few micrometers to a few hundred micrometers. For example, with reference to FIGS. 2 and 3, the cross-sectional size of the normal Schlemm's canal 18 is an oval shape of a few tens of micrometers by a few hundred micrometers. The diameter of collector channels 19 and veins is a few tens of micrometers. The thickness of the juxtacanalicular tissue 17 is a few micrometers, the thickness of the trabecular meshwork 12 is around a hundred micrometers.

The control system of the integrated surgical system is further configured to instruct the laser source to modify a volume of ocular tissue within the outflow pathway to reduce a pathway resistance present in one or more of the trabecular meshwork, the Schlemm's canal, and the one or more collector channels by applying the laser beam to ocular tissue defining the volume to thereby cause photo-disruptive interaction with the ocular tissue to reduce the pathway resistance or create a new outflow pathway.

The laser source may be a femtosecond laser. Femtosecond lasers provide non-thermal photo-disruption interaction with ocular tissue to avoid thermal damage to surrounding tissue. Further, unlike other surgical methods, with femtosecond laser treatment opening surface incisions penetrating the eye can be avoided, enabling a non-invasive treatment. Instead of performing the treatment in a sterile surgical room, the non-invasive treatment can be performed in a non-sterile outpatient facility.

An additional imaging component may be included the integrated surgical system to provide direct visual observation of the irido-corneal angle along an angle of visual observation. For example, a microscope or imaging camera may be included to assist the surgeon in the process of docking the eye to the patient interface or an immobilizing device, location of ocular tissues in the eye and observing the progress of the surgery. The angle of visual observation can also be along the angled beam path 30 to the irido-corneal angle 13 through the cornea 3 and the anterior chamber 7.

Images from the OCT imaging apparatus and the additional imaging component providing visual observation, e.g. microscope, are combined on a display device such as a computer monitor. Different images can be registered and overlaid on a single window, enhanced, processed, differentiated by false color for easier understanding. Certain features are computationally recognized by a computer processor, image recognition and segmentation algorithm can be enhanced, highlighted, marked for display. The geometry of the treatment plan can also be combined and registered with imaging information on the display device and marked up with geometrical, numerical and textual information. The same display can also be used for user input of numerical, textual and geometrical nature for selecting, highlighting and marking features, inputting location information for surgical targeting by keyboard, mouse, cursor, touchscreen, audio or other user interface devices.

OCT Imaging

Figure 1:
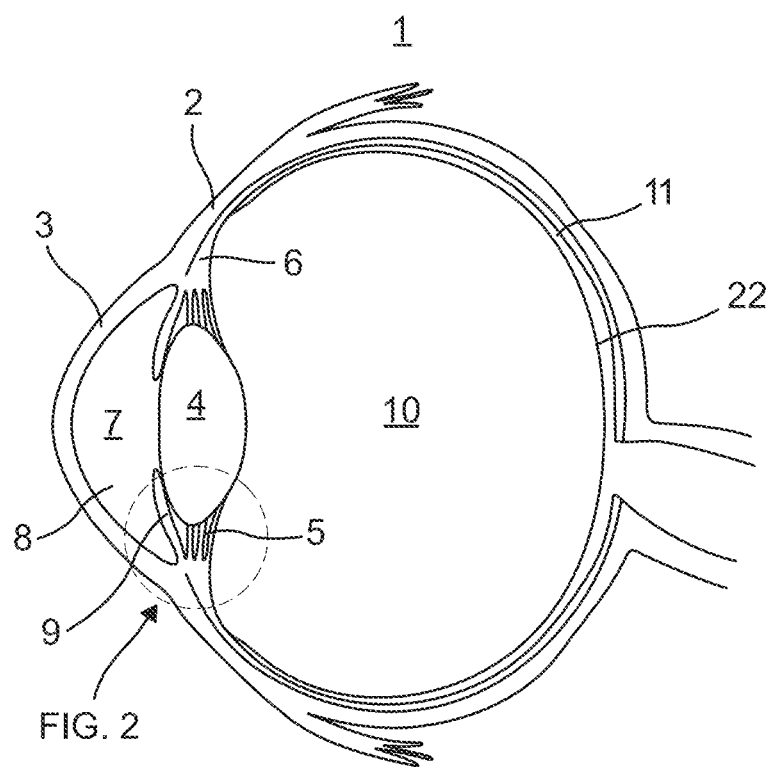
FIG. 1 is a sectional schematic illustration of a human eye and its interior anatomical structures.

The main imaging component of the integrated surgical system disclosed herein is an OCT imaging apparatus. OCT technology may be used to diagnose, locate and guide laser surgery directed to the irido-corneal angle of the eye. For example, with reference to FIGS. 1-3, OCT imaging may be used to determine the structural and geometrical conditions of the anterior chamber 7, to assess possible obstruction of the trabecular outflow pathway 40 and to determine the accessibility of the ocular tissue for treatment. As previously described, the iris 9 in a collapsed anterior chamber 7 may obstruct and close off the flow of aqueous humor 8, resulting in closed-angle glaucoma. In open-angle glaucoma, where the macroscopic geometry of the angle is normal, the permeability of ocular tissue may be affected, by blockage of tissue along the trabecular outflow pathway 40 or by the collapse of the Schlemm's canal 18 or collector channels 19.

OCT imaging can provide the necessary spatial resolution, tissue penetration and contrast to resolve microscopic details of ocular tissue. When scanned, OCT imaging can provide two-dimensional (2D) cross-sectional images of the ocular tissue. As another aspect of the integrated surgical system, 2D cross-sectional images may be processed and analyzed to determine the size, shape and location of structures in the eye for surgical targeting. It is also possible to reconstruct three-dimensional (3D) images from a multitude of 2D cross-sectional images but often it is not necessary. Acquiring, analyzing and displaying 2D images is faster and can still provide all information necessary for precise surgical targeting.

OCT is an imaging modality capable of providing high resolution images of materials and tissue. Imaging is based on reconstructing spatial information of the sample from spectral information of scattered light from within the sample. Spectral information is extracted by using an interferometric method to compare the spectrum of light entering the sample with the spectrum of light scattered from the sample. Spectral information along the direction that light is propagating within the sample is then converted to spatial information along the same axis via the Fourier transform. Information lateral to the OCT beam propagation is usually collected by scanning the beam laterally and repeated axial probing during the scan. 2D and 3D images of the samples can be acquired this way. Image acquisition is faster when the interferometer is not mechanically scanned in a time domain OCT, but interference from a broad spectrum of light is recorded simultaneously, this implementation is called a spectral domain OCT. Faster image acquisition may also be obtained by scanning the wavelength of light rapidly from a wavelength scanning laser in an arrangement called a swept-source OCT.

The axial spatial resolution limit of the OCT is inversely proportional to the bandwidth of the probing light used. Both spectral domain and swept source OCTs are capable of axial spatial resolution below 5 micrometers (μm) with sufficiently broad bandwidth of 100 nanometers (nm) or more. In the spectral domain OCT, the spectral interference pattern is recorded simultaneously on a multichannel detector, such as a charge coupled device (CCD) or complementary metal oxide semiconductor (CMOS) camera, while in the swept source OCT the interference pattern is recorded in sequential time steps with a fast optical detector and electronic digitizer. There is some acquisition speed advantage of the swept source OCT but both types of systems are evolving and improving rapidly, and resolution and speed is sufficient for purposes of the integrated surgical system disclosed herein. Stand-alone OCT systems and OEM components are now commercially available from multiple vendors, such as Optovue Inc., Fremont, Calif., Topcon Medical Systems, Oakland, N.J., Carl Zeiss Meditec AG, Germany, Nidek, Aichi, Japan, Thorlabs, Newton, N.J., Santec, Aichi, Japan, Axsun, Billercia, Mass., and other vendors.

Femtosecond Laser Source

The preferred surgical component of the integrated surgical system disclosed herein is a femtosecond laser. A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam. The process can also be used in weakly absorbing or weakly scattering tissue. While femtosecond lasers with photo-disruptive interactions have been successfully used in ophthalmic surgical systems and commercialized in other ophthalmic laser procedures, none have been used in an integrated surgical system that accesses the irido-corneal angle.

In known refractive procedures, femtosecond lasers are used to create corneal flaps, pockets, tunnels, arcuate incisions, lenticule shaped incisions, partial or fully penetrating corneal incisions for keratoplasty. For cataract procedures the laser creates a circular cut on the capsular bag of the eye for capsulotomy and incisions of various patterns in the lens for braking up the interior of the crystalline lens to smaller fragments to facilitate extraction. Entry incisions through the cornea opens the eye for access with manual surgical devices and for insertions of phacoemulsification devices and intra-ocular lens insertion devices. Several companies have commercialized such surgical systems, among them the IntraLase system now available from Johnson & Johnson Vision, Santa Ana, Calif., The LenSx and WaveLight systems from Alcon, Fort Worth, Tex., other surgical systems from Bausch and Lomb, Rochester, N.Y., Carl Zeiss Meditec AG, Germany, Ziemer, Port, Switzerland, and LENSAR, Orlando, Fla.

These existing systems are developed for their specific applications, for surgery in the cornea, and the crystalline lens and its capsular bag and are not capable of performing surgery in the irido-corneal angle 13 for several reasons. First, the irido-corneal angle 13 is not accessible with these surgical laser systems because the irido-corneal angle is too far out in the periphery and is outside of surgical range of these systems. Second, the angle of the laser beam from these systems, which is along the optical axis 24 to the eye 1, is not appropriate to reaching the irido-corneal angle 13, where there is significant scattering and optical distortion at the applied wavelength. Third, any imaging capabilities these systems may have do not have the accessibility, penetration depth and resolution to image the tissue along the trabecular outflow pathway 40 with sufficient detail and contrast.

In accordance with the integrated surgical system disclosed herein, clear access to the irido-corneal angle 13 is provided along the angled beam path 30. The tissue, e.g., cornea 3 and the aqueous humor 8 in the anterior chamber 7, along this angled beam path 30 is transparent for wavelengths from approximately 400 nm to 2500 nm and femtosecond lasers operating in this region can be used. Such mode locked lasers work at their fundamental wavelength with Titanium, Neodymium or Ytterbium active material. Non-linear frequency conversion techniques known in the art, frequency doubling, tripling, sum and difference frequency mixing techniques, optical parametric conversion can convert the fundamental wavelength of these lasers to practically any wavelength in the above-mentioned transparent wavelength range of the cornea.

Existing ophthalmic surgical systems apply lasers with pulse durations longer than 1 ns have higher photo-disruption threshold energy, require higher pulse energy and the dimension of the photo-disruptive interaction region is larger, resulting in loss of precision of the surgical treatment. When treating the irido-corneal angle 13, however, higher surgical precision is required. To this end, the integrated surgical system may be configured to apply lasers with pulse durations from 10 femtosecond (fs) to 1 nanosecond (ns) for generating photo-disruptive interaction of the laser beam with ocular tissue in the irido-corneal angle 13. While lasers with pulse durations shorter than 10 fs are available, such laser sources are more complex and more expensive. Lasers with the described desirable characteristics, e.g., pulse durations from 10 femtosecond (fs) to 1 nanosecond (ns), are commercially available from multiple vendors, such as Newport, Irvine, Calif., Coherent, Santa Clara, Calif., Amplitude Systems, Pessac, France, NKT Photonics, Birkerod, Denmark, and other vendors.

Accessing the Irido-Corneal Angle

Figure 6:
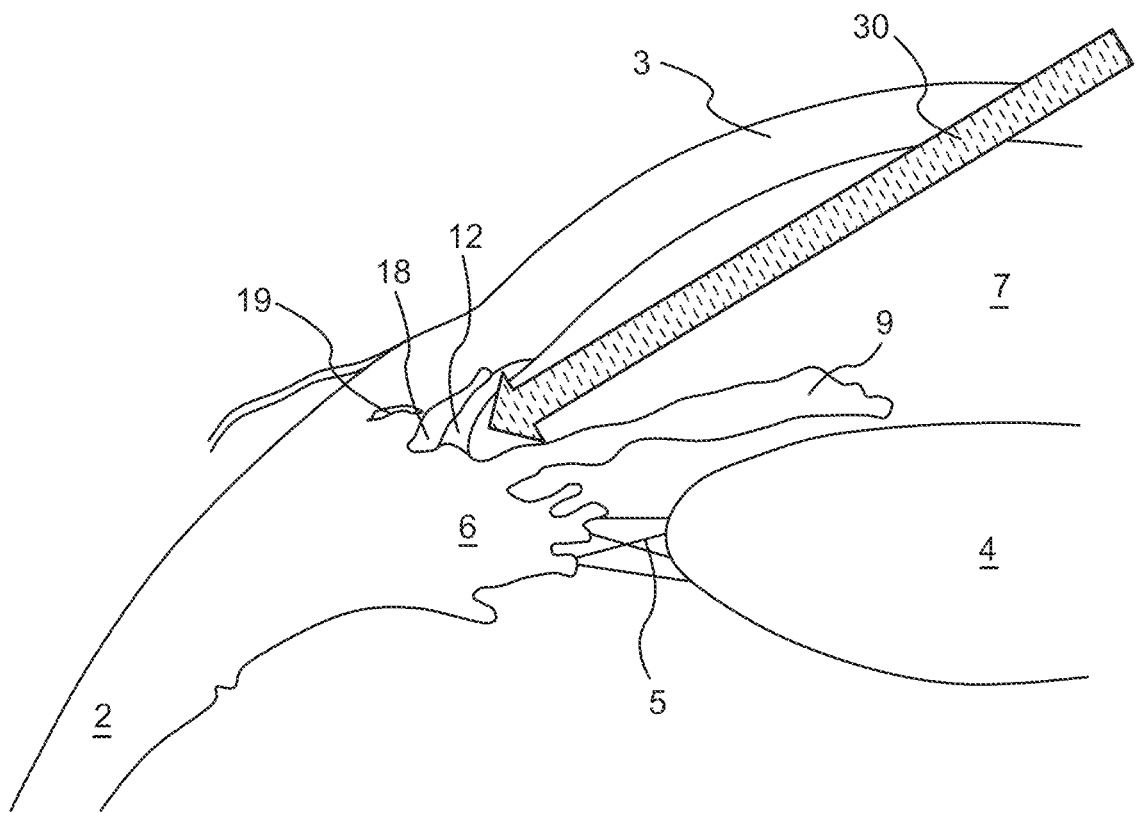
FIG. 6 is a sectional schematic illustration of an angled beam path along which one or more light beams may access the irido-corneal angle of the eye.

An important feature afforded by the integrated surgical system is access to the targeted ocular tissue in the irido-corneal angle 13. With reference to FIG. 6, the irido-corneal angle 13 of the eye may be accessed via the integrated surgical system along an angled beam path 30 passing through the cornea 3 and through the aqueous humor 8 in the anterior chamber 7. For example, one or more of an imaging beam, e.g., an OCT beam and/or a visual observation beam, and a laser beam may access the irido-corneal angle 13 of the eye along the angled beam path 30.

An optical system disclosed herein is configured to direct a light beam to an irido-corneal angle 13 of an eye along an angled beam path 30. The optical system includes a first optical subsystem and a second optical subsystem. The first optical subsystem includes a window formed of a material with a refractive index $n_w$ and has opposed concave and convex surfaces. The first optical subsystem also includes an exit lens formed of a material having a refractive index $n_x$. The exit lens also has opposed concave and convex surfaces. The concave surface of the exit lens is configured to couple to the convex surface of the window to define a first optical axis extending through the window and the exit lens. The concave surface of the window is configured to detachably couple to a cornea of the eye with a refractive index $n_c$ such that, when coupled to the eye, the first optical axis is generally aligned with the direction of view of the eye.

The second optical subsystem is configured to output a light beam, e.g., an OCT beam or a laser beam. The optical system is configured so that the light beam is directed to be incident at the convex surface of the exit lens along a second optical axis at an angle α that is offset from the first optical axis. The respective geometries and respective refractive indices $n_x$, and $n_w$ of the exit lens and window are configured to compensate for refraction and distortion of the light beam by bending the light beam so that it is directed through the cornea 3 of the eye toward the irido-corneal angle 13. More specifically, the first optical system bends the light beam to that the light beam exits the first optical subsystem and enters the cornea 3 at an appropriate angle so that the light beam progresses through the cornea and the aqueous humor 8 in a direction along the angled beam path 30 toward the irido-corneal angle 13.

Accessing the irido-corneal angle 13 along the angled beam path 30 provides several advantages. An advantage of this angled beam path 30 to the irido-corneal angle 13 is that the OCT beam and laser beam passes through mostly clear tissue, e.g., the cornea 3 and the aqueous humor 8 in the anterior chamber 7. Thus, scattering of these beams by tissue is not significant. With respect to OCT imaging, this enables the use of shorter wavelength, less than approximately 1 micrometer, for the OCT to achieve higher spatial resolution. An additional advantage of the angled beam path 30 to the irido-corneal angle 13 through the cornea 3 and the anterior chamber 7 is the avoidance of direct laser beam or OCT beam light illuminating the retina 11. As a result, higher average power laser light and OCT light can be used for imaging and surgery, resulting in faster procedures and less tissue movement during the procedure.

Another important feature provided by the integrated surgical system is access to the targeted ocular tissue in the irido-corneal angle 13 in a way that reduces beam discontinuity. To this end, the window and exit lens components of the first optical subsystem are configured to reduce the discontinuity of the optical refractive index between the cornea 3 and the neighboring material and facilitate entering light through the cornea at a steep angle.

Having thus generally described the integrated surgical system and some of its features and advantages, a more detailed description of the system and its component parts follows.

Integrated Surgical System

Figure 7:
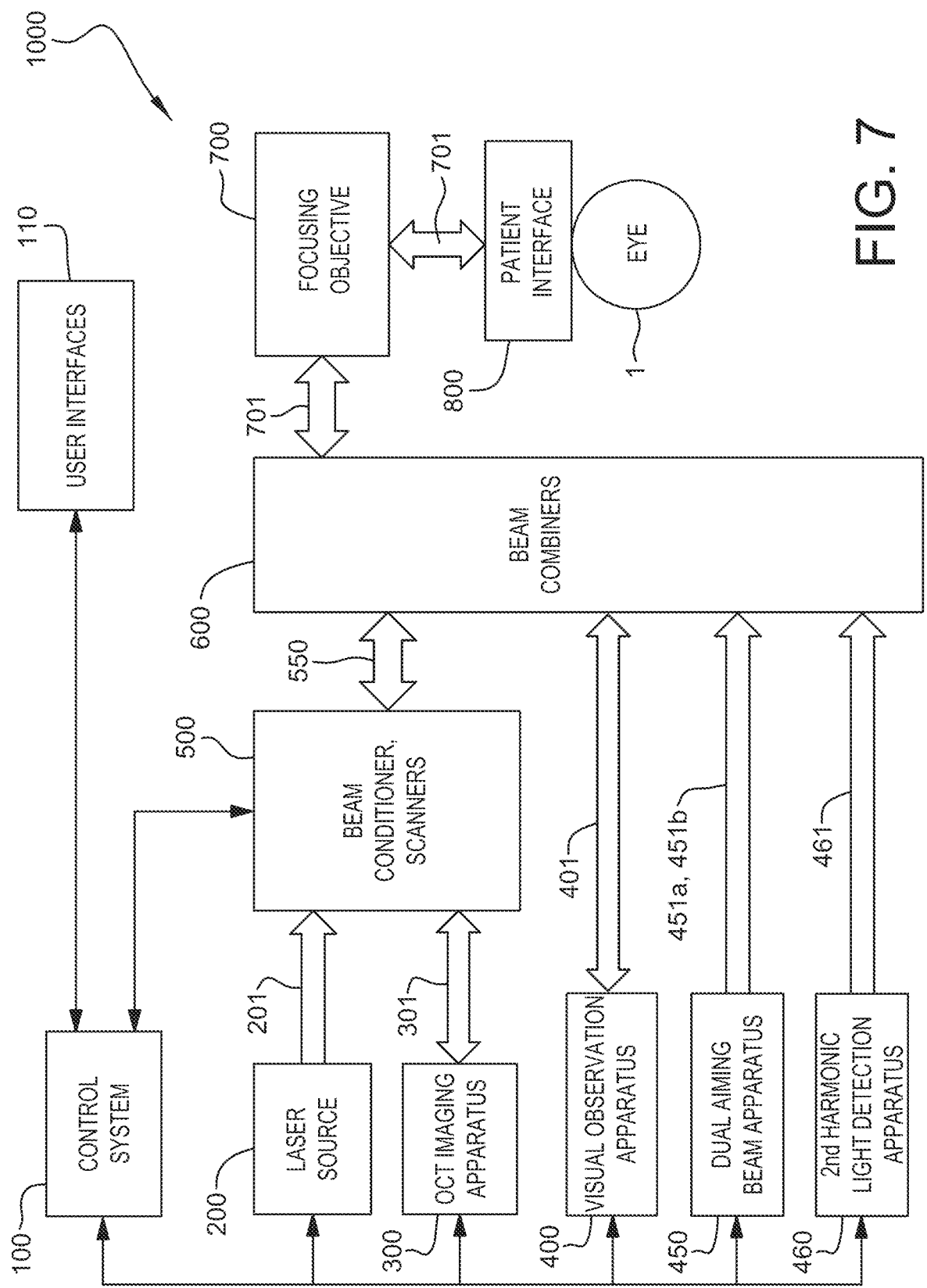
FIG. 7 is a block diagram of an integrated surgical system for non-invasive glaucoma surgery including a control system, a femtosecond laser source, an OCT imaging apparatus, a visual observation apparatus, a dual aiming beam apparatus, a second harmonic light detection apparatus, beam conditioners and scanners, beam combiners, a focusing objective, and a patient interface.

With reference to FIG. 7, an integrated surgical system 1000 for non-invasive glaucoma surgery includes a control system 100, a surgical component 200, a first imaging apparatus 300, a second imaging apparatus 400, a dual aiming beam apparatus 450, and a second harmonic light detection apparatus 460. In the embodiment of FIG. 7, the surgical component 200 is a femtosecond laser source, the first imaging apparatus 300 is an OCT imaging apparatus, and the optional second imaging apparatus 400 is a visual observation apparatus, comprising a video camera and an illumination source for viewing or capturing images of a surgical field. The dual aiming beam apparatus 450 outputs a pair of beams of light, referred to herein as aiming beams, for use in detecting a surface of ocular tissue in the surgical field. The second harmonic light detection apparatus 460 may be, for example, a photodetector configured to detect second harmonic light generated in the surgical field or a video camera instrumented with a visible filter centered near or at 515 nm (with a bandpass of 20-50 nm) that detects green light generated by surface second harmonic generation. Other components of the integrated surgical system 1000 include beam conditioners and scanners 500, beam combiners 600, a focusing objective 700, and a patient interface 800.

The control system 100 may be a single computer or and plurality of interconnected computers configured to control the hardware and software components of the other components of the integrated surgical system 1000. A user interface 110 of the control system 100 accepts instructions from a user and displays information for observation by the user. Input information and commands from the user include but are not limited to system commands, motion controls for docking the patient's eye to the system, selection of pre-programmed or live generated surgical plans, navigating through menu choices, setting of surgical parameters, responses to system messages, determining and acceptance of surgical plans and commands to execute the surgical plan. Outputs from the system towards the user includes but are not limited to display of system parameters and messages, display of images of the eye, graphical, numerical and textual display of the surgical plan and the progress of the surgery.

The control system 100 is connected to the other components 200, 300, 400, 450, 460, 500 of the integrated surgical system 1000. Signals between the control system 100 and the femtosecond laser source 200 function to control internal and external operation parameters of the laser source, including for example, power, repetition rate and beam shutter. Control and feedback signals between the control system 100 and the OCT imaging apparatus 300 function to control OCT beam scanning parameters, and the acquiring, analyzing and displaying of OCT images. Control signals between the control system 100 and the dual aiming beam apparatus 450 function to control the output of beams of light by the one or more aiming beam sources of the dual aiming beam apparatus. Control signals between the control system 100 and the visual observation apparatus 400 function to control the capturing, image processing and displaying of spots of light on tissue surfaces in the surgical field that result from the one or more beams of light output by the dual aiming beam apparatus 450. To this end, the line of sight of the visual observation apparatus 400 is aligned with the femtosecond laser and directed into the irido-corneal angle of the eye. Signals between the control system 100 and the second harmonic light detection apparatus 460 function to control the operation of the second harmonic light detection apparatus, and the detecting of second harmonic light generated by an encounter between the focus of the laser and tissue in the irido-corneal angle of the eye. To this end, the line of sight of the second harmonic light detection apparatus 460 is aligned with the femtosecond laser and directed into the irido-corneal angle of the eye. Control signals from the control system 100 to the beam conditioner and scanners 500 function to control the focus of the laser beam output by the femtosecond laser source 200. Such control may include advancing the focus of the laser beam in the direction of propagation of the laser or in the direction opposite the direction of propagation of the laser, and scanning the focus.

Laser beams 201 from the femtosecond laser source 200 and OCT beams 301 from the OCT imaging apparatus 300 are directed towards a unit of beam conditioners and scanners 500. Different kind of scanners can be used for the purpose of scanning the laser beam 201 and the OCT beam 301. For scanning transversal to a beam 201, 301, angular scanning galvanometer scanners are available for example from Cambridge Technology, Bedford, Mass., Scanlab, Munich, Germany. To optimize scanning speed, the scanner mirrors are typically sized to the smallest size, which still support the required scanning angles and numerical apertures of the beams at the target locations. The ideal beam size at the scanners is typically different from the beam size of the laser beam 201 or the OCT beam 301, and different from what is needed at the entrance of a focusing objective 700. Therefore, beam conditioners are applied before, after or in between individual scanners. The beam conditioner and scanners 500 includes scanners for scanning the beam transversally and axially. Axial scanning changes the depth of the focus at the target region. Axial scanning can be performed by moving a lens axially in the beam path with a servo or stepper motor.

The laser beam 201 and the OCT beam 301 are combined with dichroic, polarization or other kind of beam combiners 600 to reach a common target volume or surgical volume in the eye. Likewise, an illumination beam 401 from the visual observation apparatus 400 and a pair of aiming beams of light 451a, 451b from the dual aiming beam apparatus 450 are combined by dichroic, polarization or other kind of beam combiners 600 to reach the common target volume or surgical volume in the eye. In an integrated surgical system 1000 having a femtosecond laser source 200, an OCT imaging apparatus 300, a visual observation apparatus 400, and an dual aiming beam apparatus 450, the individual beams 201, 301, 401, 451a, 451b for each of these components may be individually optimized and may be collinear or non-collinear to one another. The beam combiner 600 uses dichroic or polarization beam splitters to split and recombine light with different wavelength and/or polarization. The beam combiner 600 may also include optics to change certain parameters of the individual beams 201, 301, 401, 451a, 451b such as beam size, beam angle and divergence. Integrated visual illumination, observation or imaging devices assist the surgeon in docking the eye to the system and identifying surgical locations.

To facilitate locating a focus of a femtosecond laser beam 201 at or near a target structure of ocular tissue, the second harmonic light detection apparatus 460 of the integrated surgical system 1000 generates information indicative of the presence or absence of second harmonic light in the iridocorneal angle of the eye. To this end, in one embodiment, the second harmonic light detection apparatus 460 is configured to detect for a second harmonic light beam 451 using a photodetector, and to provide an intensity profile of second harmonic generated light as a function of scan depth of the second harmonic signal as the focus of the femtosecond laser beam 201 is advanced. Details on the second harmonic light detection apparatus 460 are provided in U.S. patent application Ser. No. 16/723,883, titled "System and Method for Locating a Structure of Ocular Tissue for Glaucoma Surgery Based on Second Harmonic Light," which is hereby incorporated by reference.

To resolve ocular tissue structures of the eye in sufficient detail, the OCT imaging apparatus 300 of the integrated surgical system 1000 may provide an OCT beam having a spatial resolution of several micrometers. The resolution of the OCT beam is the spatial dimension of the smallest feature that can be recognized in the OCT image. It is determined mostly by the wavelength and the spectral bandwidth of the OCT source, the quality of the optics delivering the OCT beam to the target location in the eye, the numerical aperture of the OCT beam and the spatial resolution of the OCT imaging apparatus 300 at the target location. In one embodiment, the OCT beam of the integrated surgical system has a resolution of no more than 5 µm.

Likewise, the surgical laser beam provided by the femtosecond laser source 200 may be delivered to targeted locations with several micrometer accuracy. The resolution of the laser beam is the spatial dimension of the smallest feature at the target location that can be modified by the laser beam without significantly affecting surrounding ocular tissue. It is determined mostly by the wavelength of the laser beam, the quality of the optics delivering the laser beam to the target location in the eye, the numerical aperture of the laser beam, the energy of the laser pulses in the laser beam and the spatial resolution of the laser scanning system at the target location. In addition, to minimize the threshold energy of the laser for photo-disruptive interaction, the size of the laser spot should be no more than approximately 5 µm.

For practical embodiments, beam conditioning, scanning and combining the optical paths are certain functions performed on the laser beam 201, the OCT beam 301, the illumination beam 401, and the aiming beams of light 451a, 451b. Implementation of those functions may happen in a different order than what is indicated in FIG. 7. Specific optical hardware that manipulates the beams to implement those functions can have multiple arrangements with regards to how the optical hardware is arranged. They can be arranged in a way that they manipulate individual optical beams separately, in another embodiment one component may combine functions and manipulates different beams. For example, a single set of scanners can scan both the laser beam 201 and the OCT beam 301. In this case, separate beam conditioners set the beam parameters for the laser beam 201 and the OCT beam 301, then a beam combiner combines the two beams for a single set of scanners to scan the beams. While many combinations of optical hardware arrangements are possible for the integrated surgical system, the following section describes in detail an example arrangement.

Beam Delivery

In the following description, the term beam may—depending on the context—refer to one of a laser beam, an OCT beam, an illumination beam, or one or more aiming beams. A combined beam refers to two or more of a laser beam, an OCT beam, an illumination beam, or an aiming beam that are either collinearly combined or non-collinearly combined. Example combined beams include a combined OCT/laser beam, which is a collinear or non-colinear combination of an OCT beam and a laser beam, and a combined OCT/laser/illumination beam, which is a collinear or non-collinear combination of an OCT beam, a laser beam, and an illumination beam, and a combined OCT/laser/illumination/aiming beam, which is a collinear or non-collinear combination of an OCT beam, a laser beam, an illumination beam, and one or more aiming beams. In a collinearly combined beam, the different beams may be combined by dichroic or polarization beam splitters, and delivered along a same optical path through a multiplexed delivery of the different beams. In a non-collinear combined beam, the different beams are delivered at the same time along different optical paths that are separated spatially or by an angle between them.

In the description to follow, any of the foregoing beams or combined beams may be generically referred to as a light beam. The terms distal and proximal may be used to designate the direction of travel of a beam, or the physical location of components relative to each other within the integrated surgical system. The distal direction refers to a direction toward the eye; thus an OCT beam output by the OCT imaging apparatus moves in the distal direction toward the eye. The proximal direction refers to a direction away from the eye; thus an OCT return beam from the eye moves in the proximal direction toward the OCT imaging apparatus.

Figure 8:
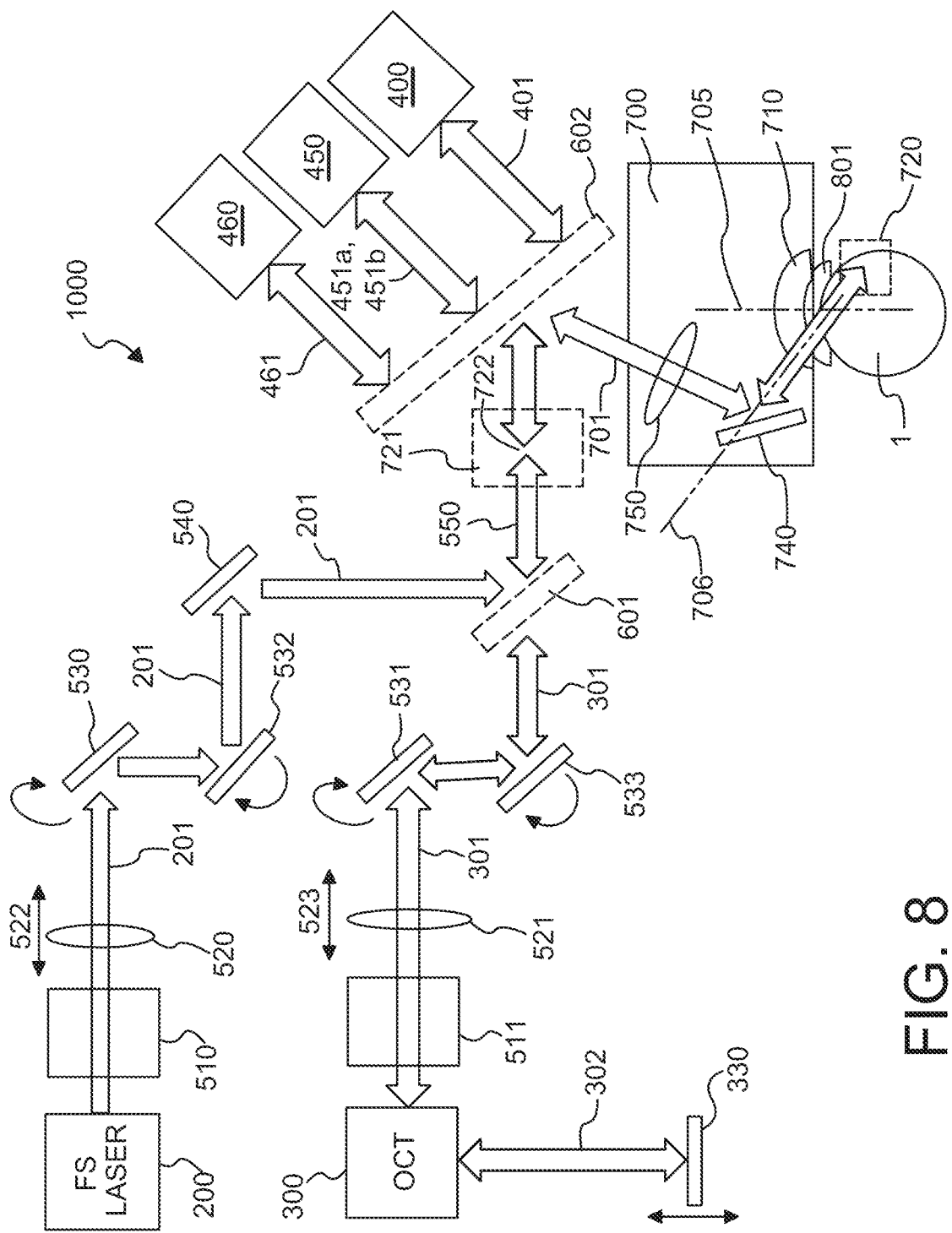
FIG. 8 is a detailed block diagram of the integrated surgical system of FIG. 7.

Referring to FIG. 8, in one embodiment, an integrated surgical system is configured to deliver each of a laser beam 201, an illumination beam 401, and a pair of aiming beams of light 451a, 451b in the distal direction toward an eye 1, and receive an illumination return beam 401 back from the eye 1. In another embodiment, an integrated surgical system is configured to deliver each of a laser beam 201, an OCT beam 301, an illumination return beam 401, and a pair of aiming beams of light 451a, 451b in the distal direction toward an eye 1, and receive each of an OCT return beam 301 and an illumination return beam 401 back from the eye 1.

In another embodiment, an integrated surgical system is configured to deliver each of a laser beam 201 and an illumination beam 401 in the distal direction toward an eye 1, and receive an illumination return beam 401 and a second harmonic light beam 461 back from the eye 1. In another embodiment, an integrated surgical system is configured to deliver each of a laser beam 201, an OCT beam 301, and an illumination return beam 401 in the distal direction toward an eye, and receive each of an OCT return beam 301, an illumination return beam 401, and a second harmonic light beam 461 back from the eye.

In another embodiment, an integrated surgical system is configured to deliver each of a laser beam 201, an illumination beam 401, a pair of aiming beams of light 451a, 451b, in the distal direction toward an eye 1, and receive an illumination return beam 401 and a second harmonic light beam 461 back from the eye 1. In another embodiment, an integrated surgical system is configured to deliver each of a laser beam 201, an OCT beam 301, an illumination beam 401, and a pair of aiming beams of light 451*a*, 451*b* in the distal direction toward an eye 1, and receive each of an OCT return beam 301, an illumination return beam 401 and a second harmonic light beam 461 back from the eye 1.

Regarding the delivery of a laser beam, a laser beam 201 output by the femtosecond laser source 200 passes through a beam conditioner 510 where the basic beam parameters, beam size, divergence are set. The beam conditioner 510 may also include additional functions, setting the beam power or pulse energy and shutter the beam to turn it on or off. After existing the beam conditioner 510, the laser beam 210 enters an axial scanning lens 520. The axial scanning lens 520, which may include a single lens or a group of lenses, is movable in the axial direction 522 by a servo motor, stepper motor or other control mechanism. Movement of the axial scanning lens 520 in the axial direction 522 changes the axial distance of the focus of the laser beam 210 at a focal point.

In a particular embodiment of the integrated surgical system, an intermediate focal point 722 is set to fall within, and is scannable in, the conjugate surgical volume 721, which is an image conjugate of the surgical volume 720, determined by the focusing objective 700. The surgical volume 720 is the spatial extent of the region of interest within the eye where imaging and surgery is performed. For glaucoma surgery, the surgical volume 720 is the vicinity of the irido-corneal angle 13 of the eye.

A pair of transverse scanning mirrors 530, 532 rotated by a galvanometer scanner scan the laser beam 201 in two essentially orthogonal transversal directions, e.g., in the x and y directions. Then the laser beam 201 is directed towards a dichroic or polarization beam splitter 540 where it is reflected toward a beam combining mirror 601 configured to combine the laser beam 201 with an OCT beam 301.

Regarding delivery of an OCT beam, an OCT beam 301 output by the OCT imaging apparatus 300 passes through a beam conditioner 511, an axially movable focusing lens 521 and a transversal scanner with scanning mirrors 531 and 533. The focusing lens 521 is used set the focal position of the OCT beam in the conjugate surgical volume 721 and the real surgical volume 720. The focusing lens 521 is not scanned for obtaining an OCT axial scan. Axial spatial information of the OCT image is obtained by Fourier transforming the spectrum of the interferometrically recombined OCT return beam 301 and reference beams 302. However, the focusing lens 521 can be used to re-adjust the focus when the surgical volume 720 is divided into several axial segments. This way the optimal imaging spatial resolution of the OCT image can be extended beyond the Rayleigh range of the OCT signal beam, at the expense of time spent on scanning at multiple ranges.

Proceeding in the distal direction toward the eye 1, after the scanning mirrors 531 and 533, the OCT beam 301 is combined with the laser beam 201 by the beam combiner mirror 601. The OCT beam 301 and laser beam 201 components of the combined laser/OCT beam 550 are multiplexed and travel in the same direction to be focused at an intermediate focal point 722 within the conjugate surgical volume 721. After having been focused in the conjugate surgical volume 721, the combined laser/OCT beam 550 propagates to a second beam combining mirror 602 where it is combined with illumination beam 401 to form a combined laser/OCT/illumination beam 701. Regarding delivery of the illumination beam 401 and the pair of aiming beams of light 451*a*, 451*b*, details of the delivery of these beams is described in U.S. patent application Ser. No. 16/781,770, titled "System and Method for Locating a Surface of Ocular Tissue for Glaucoma Surgery Based on Dual Aiming Beams," which is hereby incorporated by reference.

The combined laser/OCT/illumination/aiming beam 701 traveling in the distal direction then passes through an objective lens 750 included in the focusing objective 700, is reflected by a beam-folding mirror 740 and then passes through an exit lens 710 and a window 801 of a patient interface, where the intermediate focal point 722 of the laser beam within the conjugate surgical volume 721 is re-imaged into a focal point in the surgical volume 720. The focusing objective 700 re-images the intermediate focal point 722, through the window 801 of a patient interface, into the ocular tissue within the surgical volume 720.

A scattered OCT return beam 301 from the ocular tissue travels in the proximal direction to return to the OCT imaging apparatus 300 along the same paths just described, in reverse order. The reference beam 302 of the OCT imaging apparatus 300, passes through a reference delay optical path and return to the OCT imaging apparatus from a movable mirror 330. The reference beam 302 is combined interferometrically with the OCT return beam 301 on its return within the OCT imaging apparatus 300. The amount of delay in the reference delay optical path is adjustable by moving the movable mirror 330 to equalize the optical paths of the OCT return beam 301 and the reference beam 302. For best axial OCT resolution, the OCT return beam 301 and the reference beam 302 are also dispersion compensated to equalize the group velocity dispersion within the two arms of the OCT interferometer.

When the combined laser/OCT/illumination/aiming beam 701 is delivered through the cornea 3 and the anterior chamber 7, the combined beam passes through posterior and anterior surface of the cornea at a steep angle, far from normal incidence. These surfaces in the path of the combined laser/OCT/illumination/aiming beam 701 create excessive astigmatism and coma aberrations that need to be compensated for.

Figure 9A:
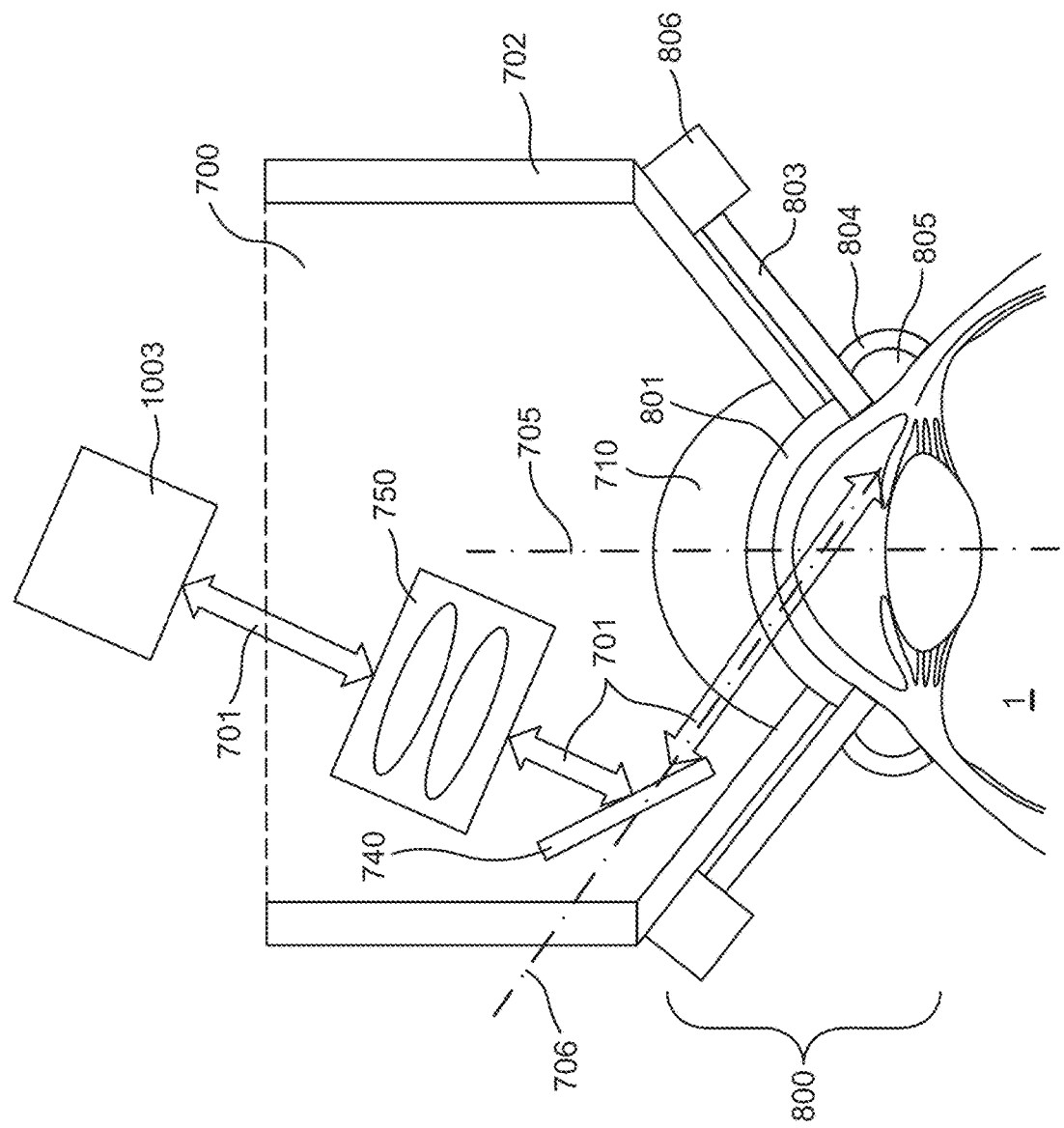

With reference to FIGS. 9*a* and 9*b*, in an embodiment of the integrated surgical system 1000, optical components of the focusing objective 700 and patient interface 800 are configured to minimize spatial and chromatic aberrations and spatial and chromatic distortions. FIG. 9*a* shows a configuration when both the eye 1, the patient interface 800 and the focusing objective 700 all coupled together. FIG. 9*b* shows a configuration when both the eye 1, the patient interface 800 and the focusing objective 700 all detached from one another.

The patient interface 800 optically and physically couples the eye 1 to the focusing objective 700, which in turn optically couples with other optic components of the integrated surgical system 1000. The patient interface 800 serves multiple functions. It immobilizes the eye relative to components of the integrated surgical system; creates a sterile barrier between the components and the patient; and provides optical access between the eye and the instrument. The patient interface 800 is a sterile, single use disposable device and it is coupled detachably to the eye 1 and to the focusing objective 700 of the integrated surgical system 1000.

Figure 9C:
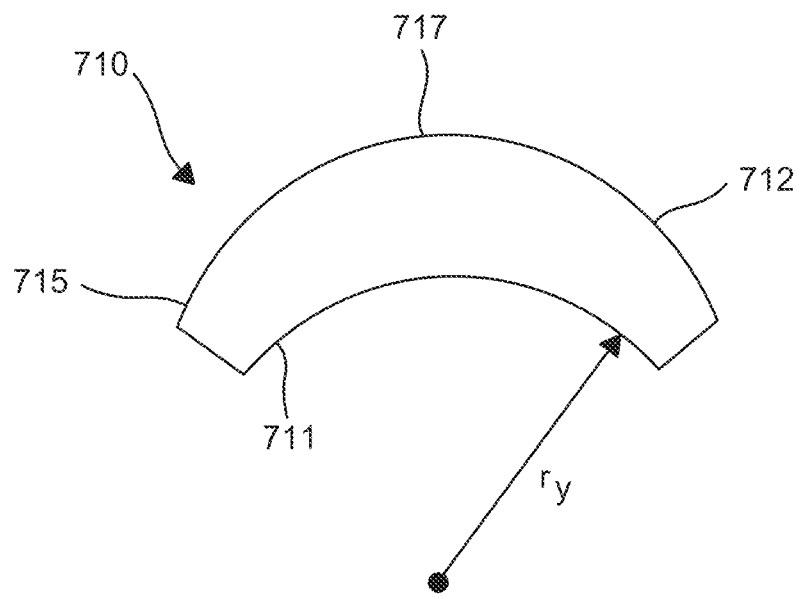
FIG. 9c is a schematic illustration of components of the focusing objective and the patient interface included in FIGS. 9a and 9b.
Figure 9C:
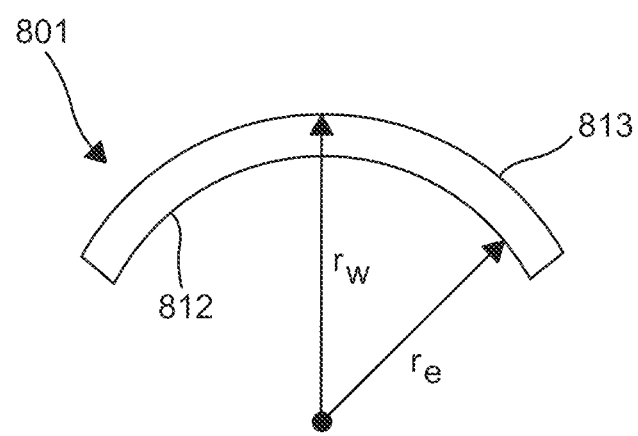

The patient interface 800 includes a window 801 having an eye-facing, concave surface 812 and an objective-facing, convex surface 813 opposite the concave surface. The window 801 thus has a meniscus form. With reference to FIG. 9c, the concave surface 812 is characterized by a radius of curvature $r_e$, while the convex surface 813 is characterized by a radius of curvature $r_w$. The concave surface 812 is configured to couple to the eye, either through a direct contact or through index matching material, liquid or gel, placed in between the concave surface 812 and the eye 1. The window 801 may be formed of glass and has a refractive index $n_w$. In one embodiment, the window 801 is formed of fused silica and has a refractive index $n_w$ of 1.45. Fused silica has the lowest index from common inexpensive glasses. Fluoropolymers such as the Teflon AF are another class of low index materials that have refractive indices lower than fused silica, but their optical quality is inferior to glasses and they are relatively expensive for high volume production. In another embodiment the window 801 is formed of the common glass BK7 and has a refractive index $n_w$ of 1.50. A radiation resistant version of this glass, BK7G18 from Schott AG, Mainz, Germany, allows gamma sterilization of the patient interface 800 without the gamma radiation altering the optical properties of the window 801.

Returning to FIGS. 9a and 9b, the window 801 is surrounded by a wall 803 of the patient interface 800 and an immobilization device, such as a suction ring 804. When the suction ring 804 is in contact with the eye 1, an annular cavity 805 is formed between the suction ring and the eye. When vacuum applied to the suction ring 804 and the cavity via a vacuum tube a vacuum pump (not shown in FIGS. 9a and 9b), vacuum forces between the eye and the suction ring attach the eye to the patient interface 800 during surgery. Removing the vacuum releases or detach the eye 1.

The end of the patient interface 800 opposite the eye 1 includes an attachment interface 806 configured to attach to the housing 702 of the focusing objective 700 to thereby affix the position of the eye relative to the other components of the integrated surgical system 1000. The attachment interface 806 can work with mechanical, vacuum, magnetic or other principles and it is also detachable from the integrated surgical system.

The focusing objective 700 includes an aspheric exit lens 710 having an eye-facing, concave surface 711 and a convex surface 712 opposite the concave surface. The exit lens 710 thus has a meniscus form. While the exit lens 710 shown in FIGS. 9a and 9b is an aspheric lens giving more design freedom, in other configurations the exit lens may be a spherical lens. Alternatively, constructing the exit lens 710 as a compound lens, as opposed to a singlet, allows more design freedom to optimize the optics while preserving the main characteristics of the optical system as presented here. With reference to FIG. 9c, the concave surface 711 is characterized by a radius of curvature $r_y$, while the convex surface 712 is characterized by an aspheric shape. The aspheric convex surface 712 in combination with the spherical concave surface 711 result in an exit lens 710 having varying thickness, with the outer perimeter edges 715 of the lens being thinner than the central, apex region 717 of the lens. The concave surface 711 is configured to couple to the convex surface 813 of the window 801. In one embodiment, the exit lens 710 is formed of fused silica and has a refractive index $n_x$ of 1.45.

Minimally Invasive Surgical Treatments

Figure 10:
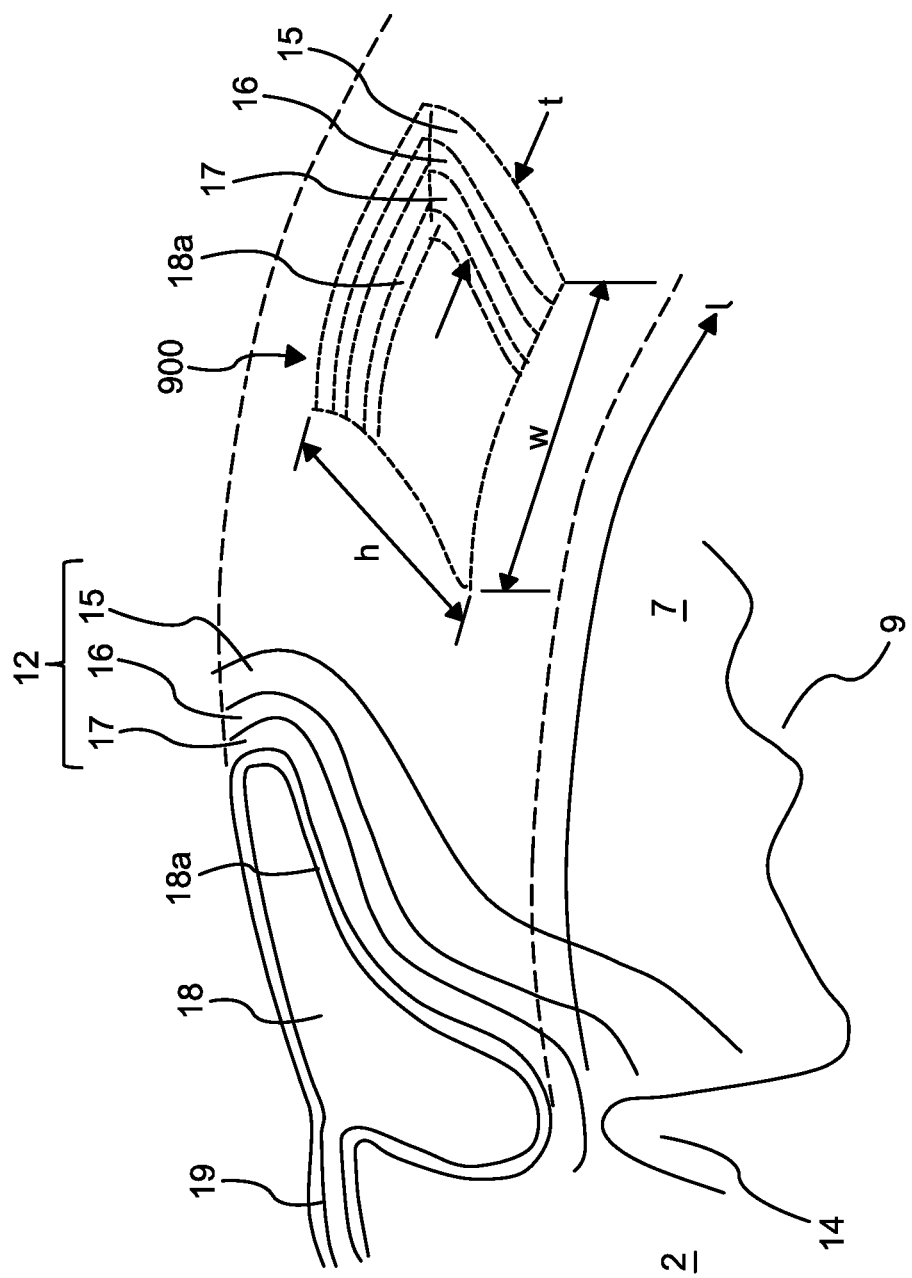
FIG. 10 is a three-dimensional schematic illustration of anatomical structures in the irido-corneal angle, including the trabecular meshwork, Schlemm's canal, a collector channel branching from the Schlemm's canal, and a surgical volume of ocular tissue to be treated by the integrated surgical system of FIG. 7.

FIG. 10 is a three-dimensional schematic illustration of anatomical structures of the eye relevant to the surgical treatment enabled by the integrated surgical system 1000. To reduce the IOP, laser treatment targets ocular tissues that affect the trabecular outflow pathway 40. These ocular tissues may include the trabecular meshwork 12, the scleral spur 14, the Schlemm's canal 18, and the collector channels 19. The trabecular meshwork 12 has three layers, the uveal 15, the corneoscleral meshwork 16, and the juxtacanalicular tissue 17. These layers are porous and permeable to aqueous, with the uveal 15 being the most porous and permeable, followed by the corneoscleral meshwork 16. The least porous and least permeable layer of the trabecular meshwork 12 is the juxtacanalicular tissue 17. The inner wall 18a of the Schlemm's canal 18, which is also porous and permeable to aqueous, has characteristics similar to the juxtacanalicular tissue 17.

Figure 12:
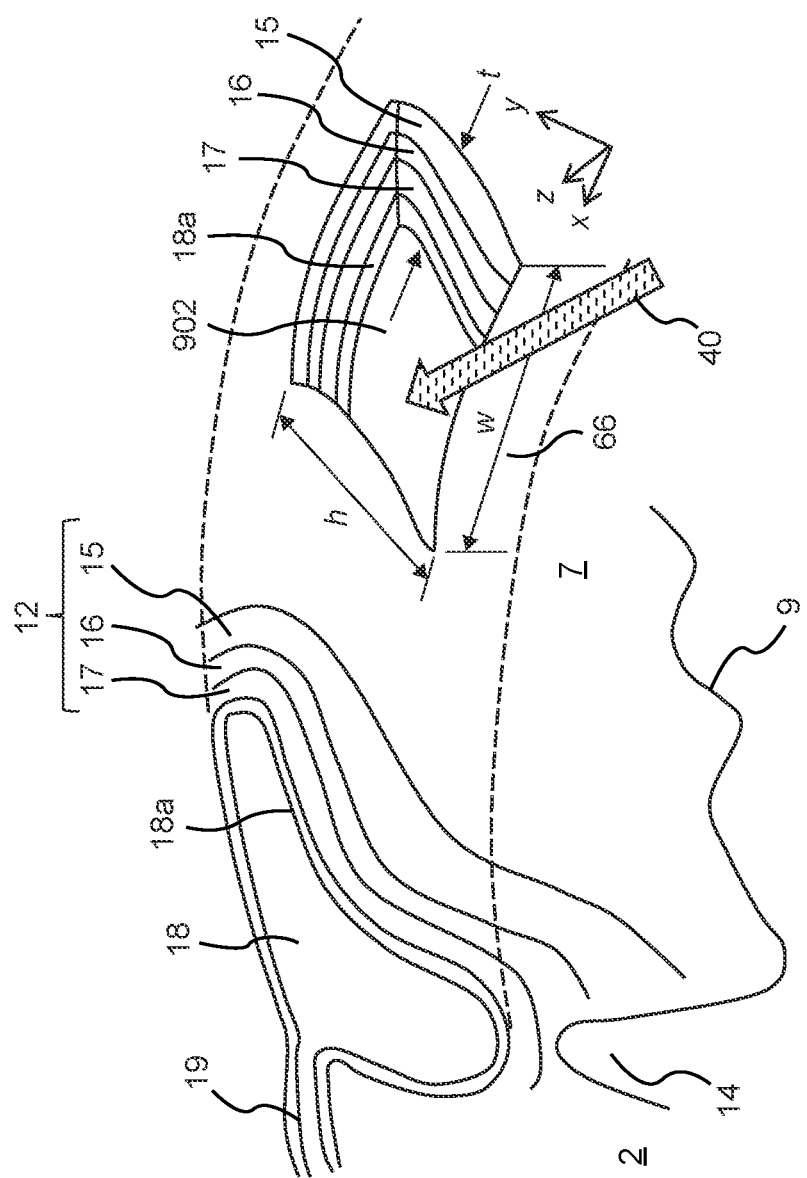
FIG. 12 is a three-dimensional schematic illustration of FIG. 10 subsequent to treatment of the surgical volume of ocular tissue by a laser based on the laser treatment pattern of FIG. 11 that forms an opening between the Schlemm's canal and the anterior chamber.

FIG. 11 includes a three-dimensional illustration of a treatment pattern P1 to be applied by the integrated surgical system 1000 to affect the surgical volume 900 of ocular tissue shown in FIG. 10, and a two-dimensional schematic illustration of the treatment pattern P1 overlaying anatomical structures to be treated. FIG. 12 is a three-dimensional schematic illustration of the anatomical structures of the eye including an opening 902 through the that results from the application of the laser treatment pattern of FIG. 11. The opening 902 provides and outflow pathway 40 that reduces the flow resistance in the ocular tissue to increase aqueous flow from the anterior chamber 7 into the Schlemm's canal 18 and thereby reduce the IOP of the eye.

Surgical treatments reduce outflow pathway resistance while minimizing ocular tissue modification through design and selection of laser treatment patterns. A treatment pattern is considered to define a collection of a laser-tissue interaction volumes, referred to herein as cells. The size of a cell is determined by the extent of the influence of the laser-tissue interaction. When the laser spots, or cells, are spaced close along a line, the laser creates a narrow, microscopic channel. A wider channel can be created by closely spacing a multitude of laser spots within the cross section of the channel. The arrangement of the cells may resemble the arrangement of atoms in a crystal structure.

With reference to FIG. 11, a treatment pattern P1 may be in the form of a cubic structure that encompasses individual cells arranged in regularly spaced rows, columns and sheets or layers. The treatment pattern P1 may be characterized by x, y, z dimensions, with x, y, z coordinates of the cells being calculated sequentially from neighbor to neighbor in the order of a column location (x coordinate), a row location (y coordinate), and a layer location (z coordinate). A treatment pattern P1 as such, defines a three-dimensional model of ocular tissue to be modified by a laser or a three-dimensional model of ocular fluid to be affected by a laser.

A treatment pattern P1 is typically defined by a set of surgical parameters. The surgical parameters may include one or more of a treatment area A that represents a surface area or layer of ocular tissue through which the laser will travel. The treatment area A is determined by the treatment height, h, and the lateral extent of the treatment, w. A treatment thickness t that represents the level to which the laser will cut into the ocular tissue from the distal extent or border of the treatment volume at or near Schlemm's canal 18 to the proximal extent or border at or near the surface of the trabecular meshwork 12. Thus, a laser applied in accordance with a treatment pattern may affect or produce a surgical volume that resembles the three-dimensional model of the treatment pattern, or may affect fluid located in an interior of an eye structure resembled by the three-dimensional model. In one example, a treatment pattern P1 may have a lateral or circumferential extent, w=1000 μm, a height, h=200 μm, and a thickness, t=500 μm.

Additional surgical parameters define the placement of the surgical volume or affected volume within the eye. For example, with reference to FIGS. 10 and 11, placement parameters may include one or more of a location l that represents where the treatment is to occur relative to the circumferential angle of the eye, and a treatment depth d that represents a position of the three-dimensional model of ocular tissue or ocular fluid within the eye relative to a reference eye structure. In the following, the treatment depth d is shown and described relative to the region where the anterior chamber 7 meets the trabecular meshwork 12. Together, the treatment pattern and the placement parameters define a treatment plan.

A femtosecond laser provides highly localized, non-thermal photo-disruptive laser-tissue interaction with minimal collateral damage to surrounding ocular tissue. Photo-disruptive interaction of the laser is utilized in optically transparent tissue. The principal mechanism of laser energy deposition into the ocular tissue is not by absorption but by a highly nonlinear multiphoton process. This process is effective only at the focus of the pulsed laser where the peak intensity is high. Regions where the beam is traversed but not at the focus are not affected by the laser. Therefore, the interaction region with the ocular tissue is highly localized both transversally and axially along the laser beam.

With reference to FIGS. 10 and 11, in accordance with embodiments disclosed herein a surgical volume 900 of ocular tissue to be treated is identified by the integrated surgical system 1000 and a treatment pattern P1 corresponding to the surgical volume is designed by the integrated surgical system. Alternatively, the treatment pattern P1 may be designed first, and then an appropriate surgical volume 900 for applying the treatment pattern may be identified. The surgical volume 900 of ocular tissue may comprise portions of the trabecular meshwork 12 and the Schlemm's canal 18. For example, the surgical volume 900 of ocular tissue shown in FIG. 11 includes portions of the uveal 15, the corneoscleral meshwork 16, the juxtacanalicular tissue 17, and the inner wall 18a of the Schlemm's canal 18. The treatment pattern P1 defines a laser scanning procedure whereby a laser is focused at different depth locations in ocular tissue and then scanned in multiple directions to affect a three-dimensional volume of tissue comprising multiple sheets or layers of affected tissue.

With reference to FIGS. 11 and 12, during a laser scanning procedure, a surgical laser 701 may scan ocular tissue in accordance with the treatment pattern P1 to form an opening 902 that extends from the anterior chamber 7, through each of the uveal 15, the corneoscleral meshwork 16, the juxtacanalicular tissue 17 of the trabecular meshwork 12, and the inner wall 18a of the Schlemm's canal 18. While the example opening 902 in FIG. 12 is depicted as a continuous, single lumen defining a fluid pathway, the opening may be defined an arrangement of adjacent pores forming a sponge like structure defining a fluid pathway or a combination thereof. While the example opening 902 in FIG. 12 is in the shape of a cube, the opening may have other geometric shapes.

The movement of the laser as it scans to affect the surgical volume 900 follows the treatment pattern P1, which is defined by a set of surgical parameters that include a treatment area A and a thickness t. The treatment area A is defined by a width w and a height h. The width may be defined in terms of a measure around the circumferential angle. For example, the width w may be defined in terms of an angle, e.g., 90 degrees, around the circumferential angle.

Referring to FIGS. 10 and 11, an initial placement of the laser focus within the eye is defined by a set of placement parameters, including a depth d and a location l. The location l defines a point around the circumferential angle of the eye at which laser treatment will begin, while the depth d defines a point between the anterior chamber 7 and the Schlemm's canal 18 where the laser treatment begins or ends. The depth d is measured relative to the region where the anterior chamber 7 meets the trabecular meshwork 12. Thus, a first point that is closer to the Schlemm's canal 18 side of the trabecular meshwork 12 may be described as being deeper than a second point that is closer to the anterior chamber 7 side of the trabecular meshwork 12. Alternatively, the second point may be described as being shallower than the first point.

With reference to FIG. 12, the opening 902 resulting from laser application of the treatment pattern P1 resembles the surgical volume 900 and is characterized by an area A and thickness t similar to those of the surgical volume and the treatment pattern. The thickness t of the resulting opening 902 extends from the anterior chamber 7 and through the inner wall 18a of the Schlemm's canal 18, while the area A defines the cross-section size of the opening 902.

In accordance with embodiments disclosed herein, during a laser scanning procedure, a laser focus is moved to different depths d in ocular tissue and then scanned in two lateral dimensions or directions as defined by a treatment pattern P1 to affect a three-dimensional volume 900 of ocular tissue comprising multiple sheets or layers of affected tissue. The two lateral dimensions are generally orthogonal to the axis of movement of the laser focus. With reference to FIG. 12, the movement of a laser focus during laser scanning is described herein with reference to x, y, and z directions or axes, wherein: 1) movement of the laser focus to different depths d through the thickness t of treatment pattern P1 or the volume 900 of tissue corresponds to movement of the focus along the z axis, 2) movement of the laser focus in two dimensions or directions orthogonal to the z axis corresponds to movement of the laser focus along the width w of the treatment pattern P1 or the volume 900 of tissue in the x direction, and movement of the laser focus along the height h of the treatment pattern P1 or the volume 900 of tissue in the y direction.

As used herein scanning of the laser focus generally corresponds to a raster type movement of the laser focus in the x direction, the y direction, and the z direction. The laser focus may be located at a point in the z direction and then raster scanned in two dimensions or directions, in the x direction and the y direction. The focal point of the laser in the z direction may be referred to as a depth d within the treatment pattern P1 or the volume 900 of tissue. The two-direction raster scanning of the laser focus defines a layer of laser scanning, which in turn produces a layer of laser-affected tissue.

During laser scanning, pulse shots of a laser are delivered to tissue within the volume of ocular tissue corresponding to the treatment pattern P1. Because the laser interaction volume is small, on the order of a few micrometers (μm), the interaction of ocular tissue with each laser shot of a repetitive laser breaks down ocular tissue locally at the focus of the laser. Pulse duration of the laser for photo-disruptive interaction in ocular tissue can range from several femtoseconds to several nanoseconds and pulse energies from several nanojoules to tens of microjoules. The laser pulses at the focus, through multiphoton processes, breaks down chemical bonds in the molecules, locally photo-dissociate tissue material and create gas bubbles in wet tissue. The breakdown of tissue material and mechanical stress from bubble formation fragments the tissue and create clean continuous cuts when the laser pulses are laid down in proximity to one another along geometrical lines and surfaces.

Table 1 includes examples of treatment pattern parameters and surgical laser parameters for treating tissue. The range of the parameter set is limited by practical ranges for the repetition rate of the laser and the scanning speed of the scanners.

TABLE 1

| Tissue treated | Treatment pattern dimensions w[mm], h[mm], t[mm] | Opening cross section A [mm²] | Cell size w[μm], h[μm], t[μm] | Laser average power [W] | Laser repetition rate [kHz] | Laser pulse energy [μJ] | Procedure time [s] |
|---|---|---|---|---|---|---|---|
| Trabecular meshwork | 1.5, 0.2, 0.2 | 0.3 | 3, 3, 3 | 0.9 | 300 | 3 | 7.4 |
| Trabecular meshwork | 2, 0.2, 0.2 | 0.4 | 4, 4, 4 | 1 | 200 | 5 | 6.3 |

Alignment and Diagnostic Device

Figure 13:
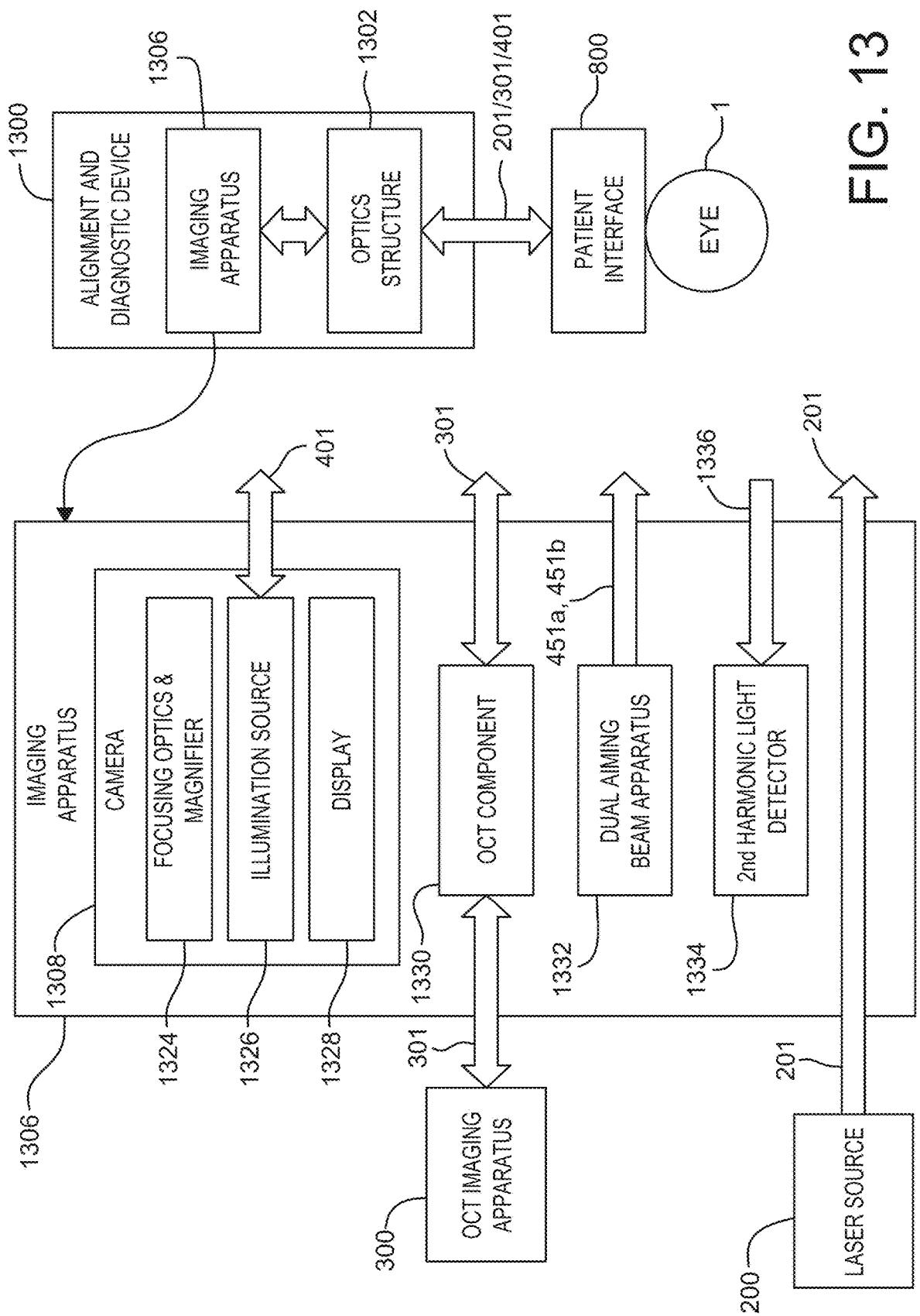
FIG. 13 is a block diagram of an alignment and diagnostic device for visualizing an irido-corneal angle of an eye including an imaging apparatus and an optics structure that couples to a patient interface.
Figure 14A:
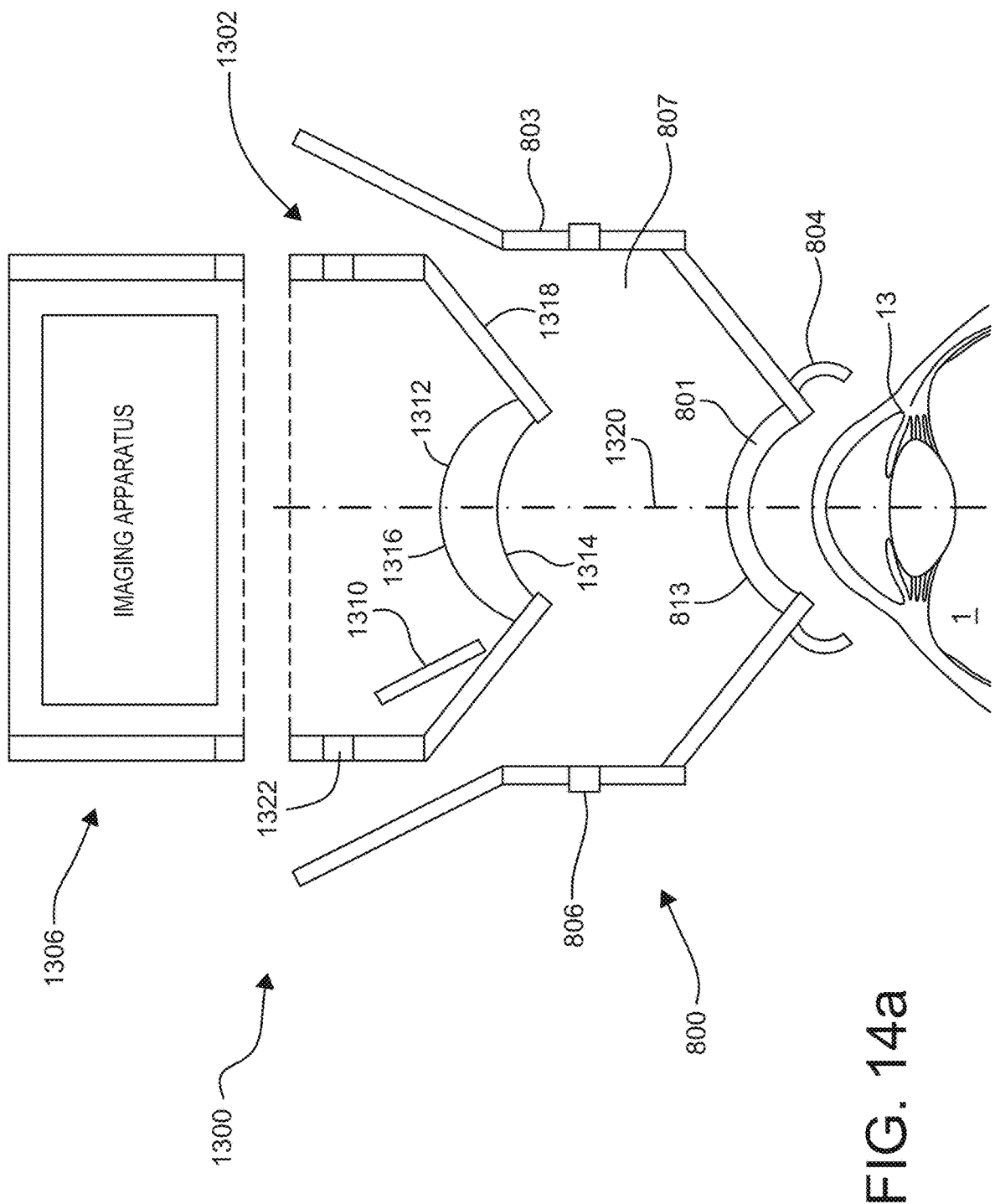
FIGS. 14a and 14b are schematic illustrations of an alignment and diagnostic device for visualizing an irido-corneal angle of an eye.
Figure 14B:
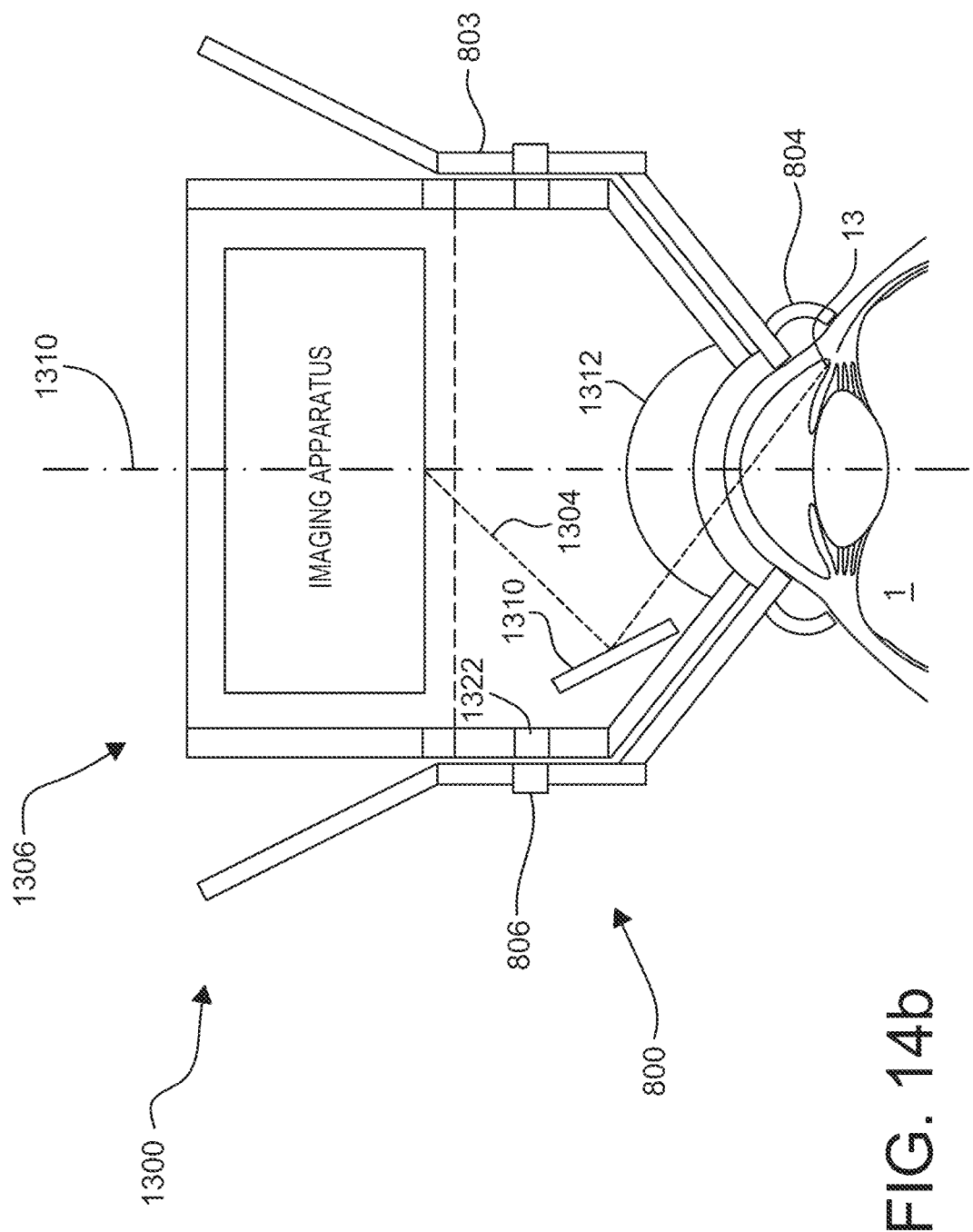

FIG. 13 is a block diagram of an alignment and diagnostic device 1300 for visualizing an irido-corneal angle 13 of an eye 1. FIGS. 14a and 14b are schematic illustrations of the alignment and diagnostic device 1300. The device 1300 includes an optics structure 1302 and an imaging apparatus 1306. The optics structure 1302 is configured to engage with a patient interface 800 placed on the eye 1 to provide a line of sight 1304 in the direction of the irido-corneal angle 13, and to subsequently disengage from the patient interface. The imaging apparatus 1306 is associated with the optics structure 1302 and has at least one imaging component aligned with the line of sight 1304 to enable capturing an image of the eye 1 including the irido-corneal angle 13. The imaging component may be a camera 1308, an OCT component 1330 of an OCT imaging apparatus 300, a dual aiming beam apparatus 1332, or a second harmonic light detection apparatus 1334.

With reference to FIGS. 14a and 14b, the optics structure 1302 includes one or more facet mirrors 1310 that provide a view of the irido-corneal angle 13 through an exit lens 1312 of the optics structure. In one configuration, the exit lens 1312 is an aspheric exit lens having an eye-facing, concave surface 1314 and a convex surface 1316 opposite the concave surface. The exit lens 1312 thus has a meniscus form. Similar to the exit lens 710 shown in FIGS. 9a and 9b, the exit lens 1312 of the optics structure 1302 may be an aspheric lens giving more design freedom, in other configurations the exit lens may be a spherical lens. Similar to the exit lens 710 shown in FIGS. 9a and 9b, the exit lens 1312 of the optics structure 1302 may have a concave surface 1314 characterized by a radius of curvature $r_y$, while the convex surface 1316 is characterized by an aspheric shape. The aspheric convex surface 1316 in combination with the spherical concave surface 1314 result in an exit lens 1312 having varying thickness, with the outer perimeter edges of the lens being thinner than the central, apex region of the lens. The concave surface 1314 is configured to couple to the convex surface 813 of the window 801.

While the optics structure 1302 illustrated in FIGS. 14a and 14b has a single facet mirror 1310, additional facet mirrors may be included to provide images of the eye around a larger portion of the circumferential extent of the irido-corneal angle. Accordingly, in some configurations, the optics structure 1302 may be configured to provide the line of sight 1304 in the direction of the irido-corneal angle 13 around a small portion of the circumferential extent of the irido-corneal angle. For example, FIG. 15a is an illustration of an image 1502 of a circumferential extent 1504 of an irido-corneal angle of an eye captured by an optics structure 1302 having a single facet mirror 1506. The single facet mirror configuration provides a line of sight in the direction of the irido-corneal angle at the circumferential extent 1504 opposite the single facet mirror 1506.

In other configurations, the optics structure 1302 may be configured to provide lines of sight 1304 in the direction of the irido-corneal angle 13 around a larger circumferential extent of the irido-corneal angle. For example, FIG. 15b is an illustration of four images 1508, 1510, 1512, 1514 of portions of an irido-corneal angle 13 captured by an optics structure 1302 having four facet mirrors (not shown). Each facet mirror provides a line of sight in the direction of the irido-corneal angle at a portion of the circumferential extent 1516 opposite the facet mirror.

Figure 16:
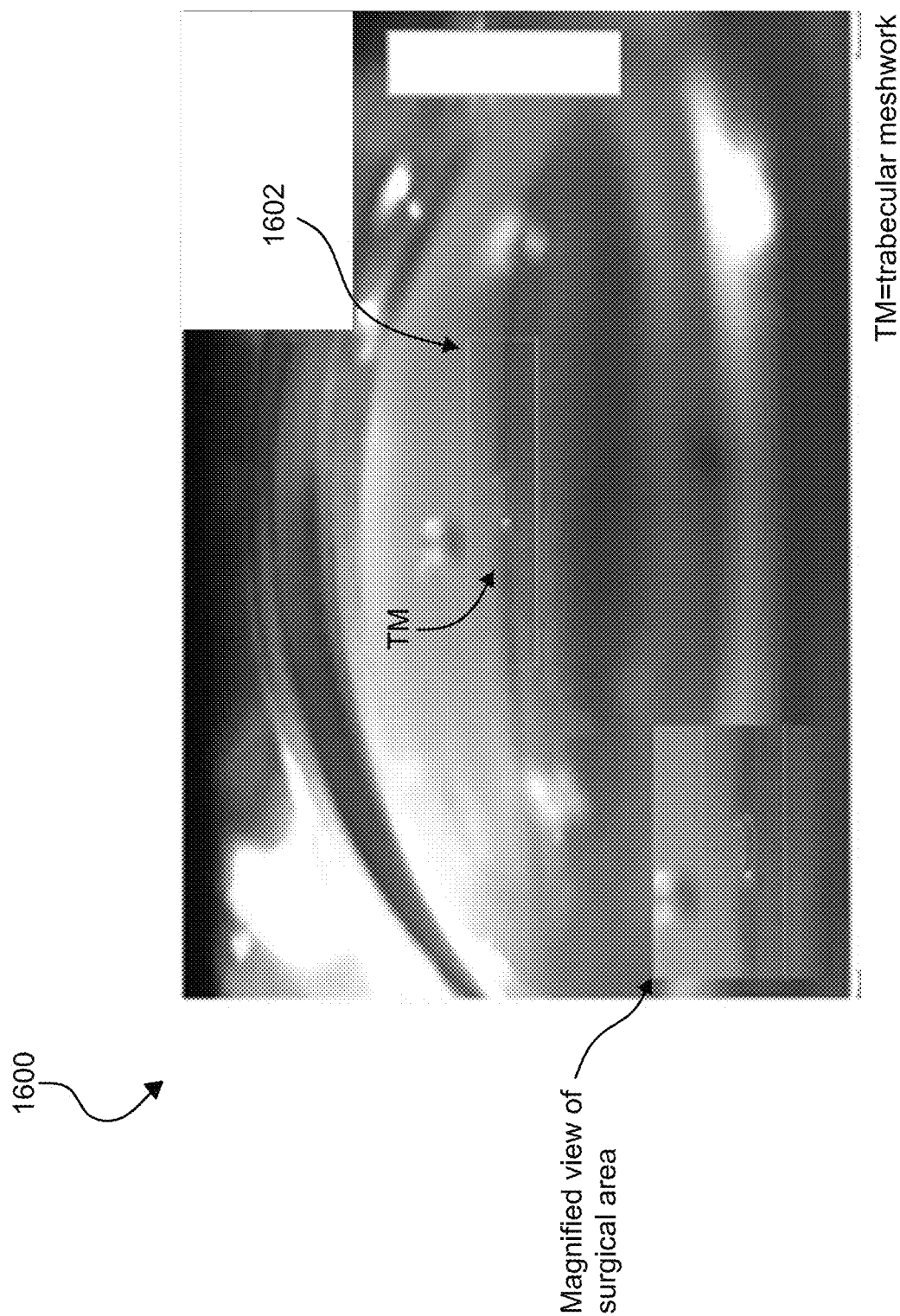
FIG. 16 is an image of a portion of an irido-corneal angle of an eye captured by a camera of an alignment and diagnostic device.

Returning to FIGS. 13, 14a and 14b, in one embodiment of the alignment and diagnostic device 1300 the imaging apparatus 1306 is a visual observation apparatus, e.g., a camera 1308. The camera 1308 includes an illumination source 1326 configured to output light 401 in the direction of the line of sight into the irido-corneal angle 13. The camera 1308 further includes a focusing optics and magnifier 1324 configured to focus and magnify the image captured by the camera. The camera 1306 may also include a display 1328 for displaying an image captured by the camera. FIG. 16 is an example image 1600 of a portion of an irido-corneal angle captured by a camera 1306 together with a surgical overlay mark 1602. The surgical overlay mark 1602 may correspond to an area that may be treated by the surgical laser of the integrated surgical system 1000.

In another embodiment of the alignment and diagnostic device 1300 the imaging apparatus 1306 is configured to be coupled to an OCT imaging apparatus 300 remote from the alignment and diagnostic device 1300 and includes one or more OCT components 1330. The one or more OCT components 1330 may be, for example, an OCT scanner head and an interface configured to couple the OCT scanner head to the remote OCT imaging apparatus 300 and to receive an OCT beam 301 from the apparatus. The remote OCT apparatus 300 may be part of an integrated surgical system 1000, which may include a display for displaying OCT images. FIGS. 17a and 17b are example images 1700, 1706 of a portion of an irido-corneal angle captured by the one or more OCT components 1330 in conjunction with the OCT imaging apparatus 300 showing the Schlemm's canal 1702 and trabecular meshwork 1704 from different OCT scan directions. These types of images may be used to locate a target surface of ocular tissue not visible in an image captured by a camera. For example, with reference to FIG. 11, target tissue of the trabecular meshwork 12 at a depth d between the anterior chamber 7 and the Schlemm's canal 18 may be visible in an OCT image.

In another embodiment of the alignment and diagnostic device 1300 the imaging apparatus 1306 includes a dual aiming beam mechanism 1332 and optics configured to transmit a first beam of light 451a at a first wavelength and a second beam light 451b at a second wavelength different then the first wavelength in the direction of the line of sight into the irido-corneal angle 13. In one configuration, the dual aiming beam mechanism 1332 includes one or more fiber optic cables. Spots generated by a first beam of light and a second beam of light may be used to locate a surface of ocular tissue as disclosed in U.S. patent application Ser. No. 16/781,770, titled "System and Method for Locating a Surface of Ocular Tissue for Glaucoma Surgery Based on Dual Aiming Beams." These spots may be displayed on a display, such as the display 1328 of the camera 1308, or a display remote from the alignment and diagnostic device 1300, and may be used to locate a target surface of ocular tissue not visible in an image captured by a camera. For example, with reference to FIG. 11, a target surface corresponding to the surface of the uveal 15 facing the anterior chamber 7 may be located using the dual aiming beam apparatus.

In another embodiment of the alignment and diagnostic device 1300 the imaging apparatus 1306 includes a second harmonic light detection apparatus 1334. The second harmonic light detection apparatus 1334 generates information indicative of the presence or absence of second harmonic light in the irido-corneal angle of the eye that may be generated by an encounter between the focus of a laser beam 201 and ocular tissue. To this end, in one embodiment, the second harmonic light detection apparatus 1334 is configured to detect for a second harmonic light beam 1336 using a photodetector, and to provide an intensity profile of second harmonic generated light. The intensity of second harmonic generated light may be used to locate a surface of ocular tissue as disclosed in U.S. patent application Ser. No. 16/723,883, titled "System and Method for Locating a Structure of Ocular Tissue for Glaucoma Surgery Based on Second Harmonic Light." The second harmonic light may be displayed on a display, such as the display 1328 of the camera 1308, or a display remote from the alignment and diagnostic device 1300, and may be used to locate a target surface of ocular tissue not visible in an image captured by a camera. For example, with reference to FIG. 11, target tissue between the anterior chamber 7 and the Schlemm's canal 18 may be located using the second harmonic light detection apparatus 1334.

Figure 18C:
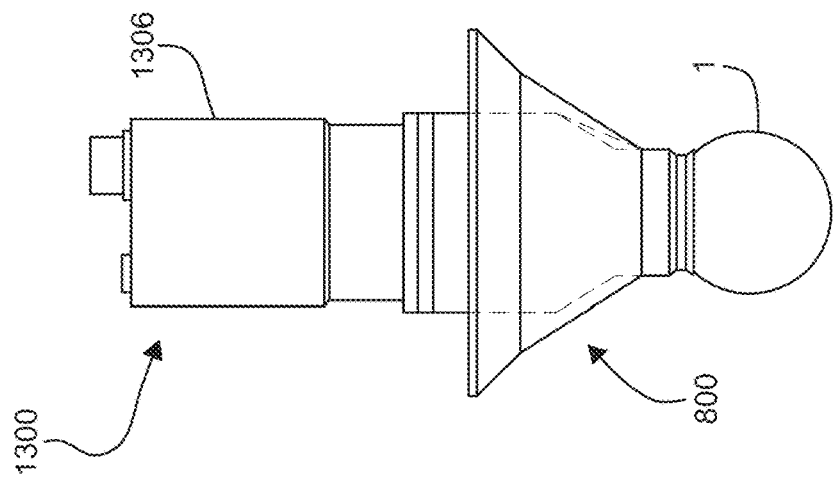
FIGS. 18a, 18b and 18c are illustrations of an alignment and diagnostic device together with a patient interface.
Figure 18B:
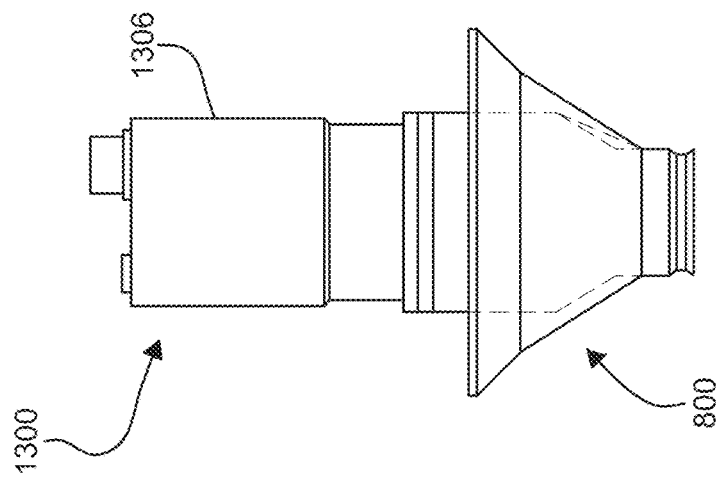
Figure 18A:
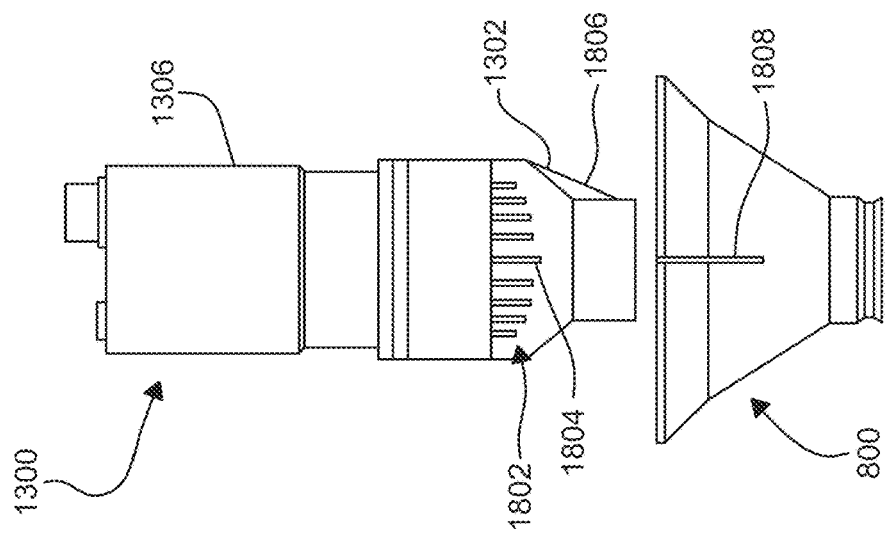

FIGS. 18a, 18b and 18c are illustrations of a first embodiment of an alignment and diagnostic device 1300 for visualizing an irido-corneal angle 13 of an eye 1. In this embodiment, the imaging apparatus 1306 and the optics structure 1302 are assembled together to form the alignment and diagnostic device 1300. For example, the imaging apparatus 1306 and the optics structure 1302 may mechanically couple together through a bayonet-style mount or a screw mechanism. In this configuration, the imaging apparatus 1306 and the optics structure 1302 may decouple from each other as need to, for example, if either requires replacement. In an alternate configuration, the imaging apparatus 1306 and the optics structure 1302 are fixedly secured together such that the alignment and diagnostic device 1300 is a single unitary structure and the component parts cannot be separated.

The optics structure 1302 is configured to mechanically couple to the patient interface 800 and to rotate relative to the patient interface together with the at least one imaging apparatus 1306 to enable the capturing of images of the irido-corneal angle 13 at various angular positions around the circumferential extent of the irido-corneal angle. To this end, and with additional reference to FIG. 14a, the patient interface 800 includes a wall 803 around the window 801 that defines an interior space 807 and the optics structure 1302 is configured to mate within the interior space. The interior space 807 of the patient interface 800 is characterized by an interior shape and the optics structure 1302 is characterized by an exterior shape similar to the interior shape. In other words, the optics structure 1302 has a form factor that fits into the patient interface 800. Furthermore, the optics structure 1302 is characterized by an exterior surface 1318 that enables rotation of the optics structure relative to the patient interface 800 about a symmetry axis 1320 extending through the optics structure and the patient interface.

With reference to FIG. 18a, the optics structure 1302 comprises a mechanism for providing a measure of the relative angular position between the optics structure and the patient interface 800. The mechanism may be a rotational registration 1802 that includes a several alignment marks 1804 spaced apart around the circumference of the housing 1806 of the optics structure 1302. The marks 1804 provide an angular scale configured to align with an alignment mark 1808 of the patient interface 800. During use of the alignment and diagnostic device 1300 the optics structure 1302 together with the imaging apparatus 1306 may be rotated relative to the patient interface 800 to obtain an image of the desired portion of the circumferential extent of the irido-corneal angle of the eye, and then rotated to another position to obtain an image of another portion of the circumferential extent of the irido-corneal angle of the eye. Rotation is particularly needed when the optics structure 1302 is configured with a single facet mirror, such as described above with reference to FIG. 14a. Upon capture of the desired image, the position of the alignment marks 1804 relative to an alignment mark 1808 of the patient interface may be recorded as a "circumferential angular position" and subsequently used to align the focusing objective 700 of the integrated surgical system 1000 relative to the patient interface 800 during a surgical procedure.

With reference to FIGS. 14a and 14b, the alignment and diagnostic device 1300 includes a locking mechanism 1322 associated with the optics structure 1302. The locking mechanism 1322 is configured to enable fixation of the optics structure 1302 relative to the patient interface 800 at various angular positions around the circumferential extent of the irido-corneal angle 13. To this end, the locking mechanism 1322 is configured to engage the attachment interface 806 of the patient interface 800. The locking mechanism 1322 may be anyone of: a vacuum port coupled to a vacuum source that establishes a vacuum between surfaces of the optics structure and the patient interface, a mechanical structure configured to engage a complimentary mechanical structure 806 of the patient interface (e.g., a bayonet mount, a mating flange, locking clips), a magnetic structure coupled to a magnetic source that establishes a magnetic force between the magnetic structure and a magnetic structure 806 of the patient interface (e.g., electromagnet on optics structure and ferromagnetic insert on patient interface), and a pneumatic element coupled to a pneumatic source, wherein the pneumatic element is configured to expand against a surface of the patient interface.

Figure 21A:
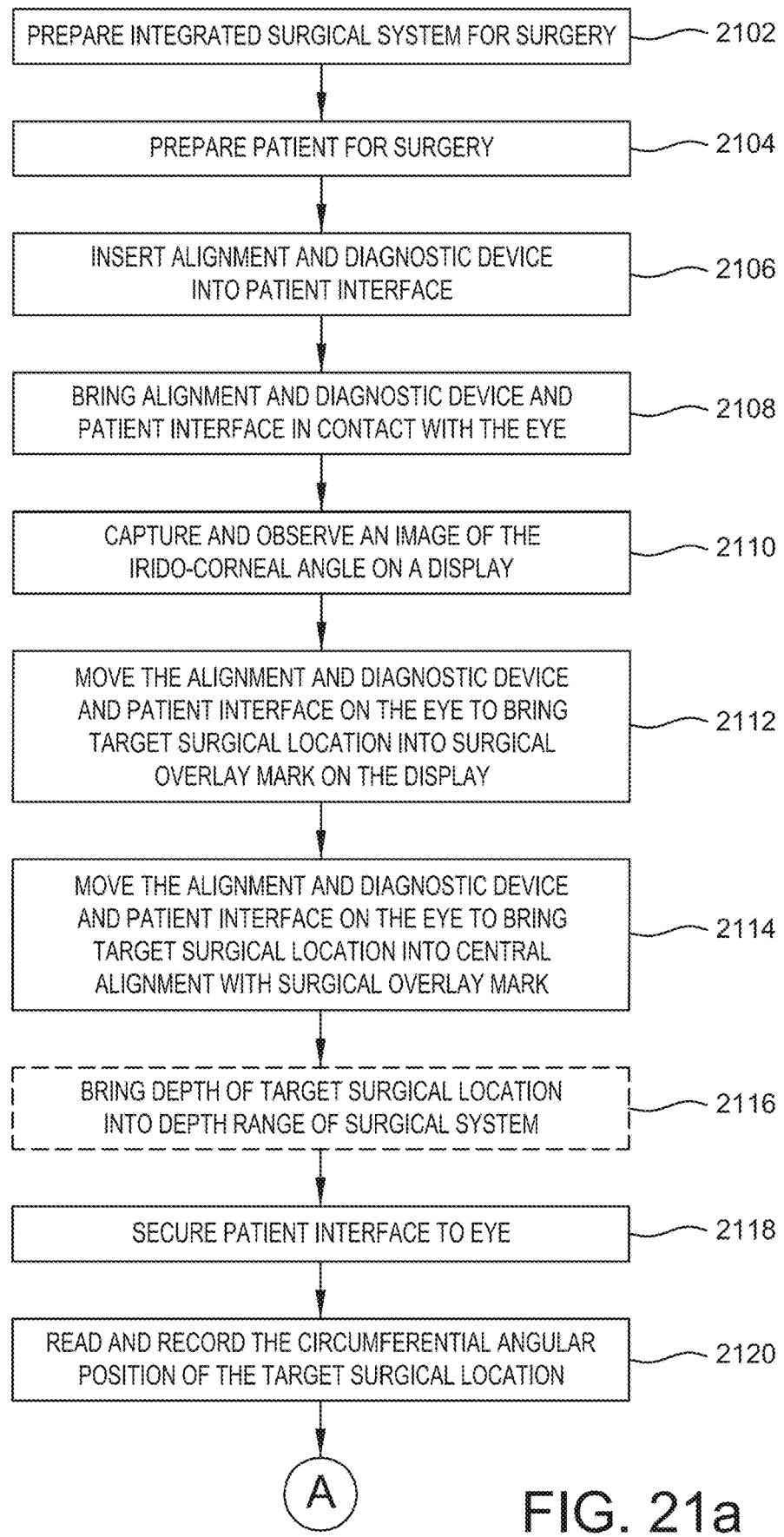
FIGS. 21a-21b are a flowchart of a method of laser surgical treatment of an eye that employs the alignment and diagnostic device of FIG. 13.
Figure 21B:
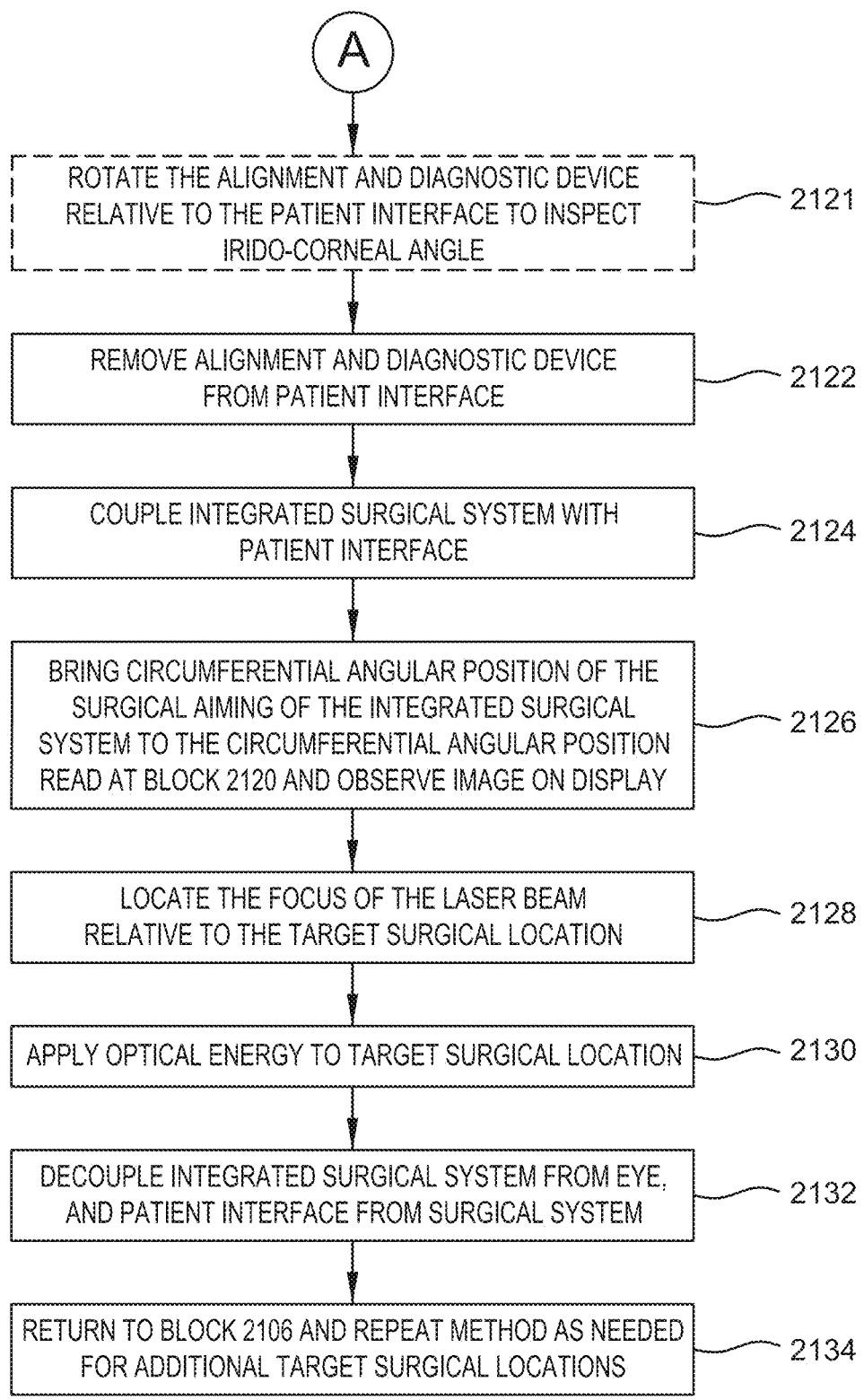

Having thus described the structure and configuration of an alignment and diagnostic device 1300, a method of laser surgical treatment of an eye 1 that employs the device is disclosed with reference to FIGS. 21a-21b. The method aligns a patient interface 800 relative to a target surgical location of the eye 1 using the alignment and diagnostic device 1300 so that a laser output by a surgical system 1000 subsequently coupled to the patient interface is directed to the target surgical location.

With reference to FIGS. 21a-21b, at block 2102, the integrated surgical system 1000 is prepared for surgery. Such preparation includes entering patient and pre-op data and a surgical plan as necessary. The surgical plan may include, for example, a treatment plan in the form of 3D CAD software file, a stereo lithography file, an image file, a plurality of image files, an spreadsheet file, or parameter values pre-entered by the surgeon.

At block 2104, the patient is prepared for surgery. Such preparation includes placing the patient on a surgical bed in supine position; applying topical anesthetic eye drops as necessary; and applying lubricant on the eye 1 as necessary.

At block 2106, and with reference to FIGS. 18a and 18b, an alignment and diagnostic device 1300 is inserted into a patient interface 800. Note that the locking mechanism 1322 of the alignment and diagnostic device 1300 shown in FIG. 14b may or may not be engaged with the patient interface 800 at this point. In cases where the alignment and diagnostic device 1300 is locked to the patient interface 800 by the locking mechanism 1322, the device and interface move together and in effect, become a single combined structure. In cases where the alignment and diagnostic device 1300 is not locked to the patient interface 800 by the locking mechanism 1322, the friction fit between the alignment and diagnostic device 1300 and the patient interface 800 may be sufficient to make the combination of the device and interface stable enough to move together like a single structure.

In either case, at block 2108, and with reference to FIG. 18c, the combination of the alignment and diagnostic device 1300 and the patient interface 800 is brought into contact with the eye 1. Note that the immobilization device 804 of the patient interface 800 shown in FIG. 14b is not engaged at this point to allow for movement of the alignment and diagnostic device 1300 together with the patient interface relative to the eye 1.

At block 2110, and with reference to FIG. 19a, an image 1900 of the irido-corneal angle 13 is captured by the imaging apparatus 1306 of the alignment and diagnostic device 1300 and displayed for observation by the user. In one embodiment, the image 1900 may be captured by a camera 1308 and presented on a display 1328 of the alignment and diagnostic device 1300. The display 1328 is configured to display a surgical overlay mark 1902 to assist in aligning the alignment and diagnostic device 1300 and patient interface 800 relative to a target surgical location 1909 at a circumferential extent of the irido-corneal angle.

In one configuration, the surgical overlay mark 1902 includes: A) a coarse surgical area (CSA) 1901 that defines a coarse area that may be treated by the surgical laser of the integrated surgical system 1000; B) a fine surgical area (FSA) overlay 1903 that defines a more fine area that can be treated by the surgical laser of the integrated surgical system 1000; C) a circumference scanning mark 1905 that indicates the length and orientation of circumferential scanning by the OCT imaging apparatus 300 coupled to the alignment and diagnostic device; and D) a transverse or azimuthal scanning mark 1907 that indicates the length and orientation of the azimuthal scanning by the OCT imaging apparatus.

The coarse surgical area overlay 1901 and the fine surgical area overlay 1903 seen in the alignment and diagnostic device 1300 are made to coincide with the coarse surgical area and the fine surgical area of the surgical laser of the integrated surgical system 1000 by scaling the relative size of the overlay areas according to the relative magnification of the alignment and diagnostic device and the magnification of the integrated surgical system 1000. Similarly, the circumference scanning mark 1905 and the azimuthal scanning mark 1907 seen in the alignment and diagnostic device 1300 are made to coincide with the circumference scanning mark and the azimuthal scanning mark of the OCT imaging apparatus 300 by scaling the relative size of the marks according to the relative magnification of the alignment and diagnostic device and the magnification of the integrated surgical system 1000.

With reference to FIGS. 19b and 19c, which are schematic representations based on the image of FIG. 19a, the image 1900 of the irido-corneal angle 13 captured by the imaging apparatus 1306 of the alignment and diagnostic device 1300 displays observable anatomical features including the ciliary body band and iris 1904, scleral spur 1906, the cornea 1908, the trabecular meshwork 1910 and Schwalbe's line 1912. The display 1328 of the alignment and diagnostic device 1300 provides the surgical overlay mark 1902 that includes the previously described CSA overlay 1901, FSA overlay 1903, circumference scanning mark 1905, and azimuthal scanning mark 1907.

Returning to FIGS. 21a-21b, at block 2112 and with reference to FIG. 19b, while continuing to observe the image of the irido-corneal angle 13 captured by the alignment and diagnostic device 1300, the combination of the alignment and diagnostic device and the patient interface 800 is moved on the eye 1 to bring an image of a circumferential extent of the irido-corneal angle and a target surgical location 1909 of the trabecular meshwork 1910 into the surgical overlay mark 1902, including the CSA overlay 1901. For example, with reference to FIG. 22a, the combination of the alignment and diagnostic device 1300 and the patient interface 800 may be moved by sliding or tilting the combination over the cornea. The combination alignment and diagnostic device 1300 together and the patient interface 800 moves relative to the eye by virtue of the eye lubricant applied. While moving the alignment and diagnostic device 1300 and the patient interface 800, physical contact between the anterior corneal surface and the patient interface is maintained.

The target surgical location 1909 to be brought into the surgical overlay mark 1902 includes a target volume of ocular tissue to be laser treated. As mention above, the coarse surgical area overlay 1901 displayed by the alignment and diagnostic device 1300 coincides with the coarse surgical area of the surgical laser of the integrated surgical system 1000. As such, orienting the alignment and diagnostic device 1300 so that the target surgical location 1909 is in the CSA overlay 1901 assures that the target volume of ocular tissue included in that segment is in the CSA of the surgical laser. Note that the alignment and diagnostic device 1300 together with the patient interface 800 will slide relative to the eye by virtue of the eye lubricant applied.

Figure 22B:
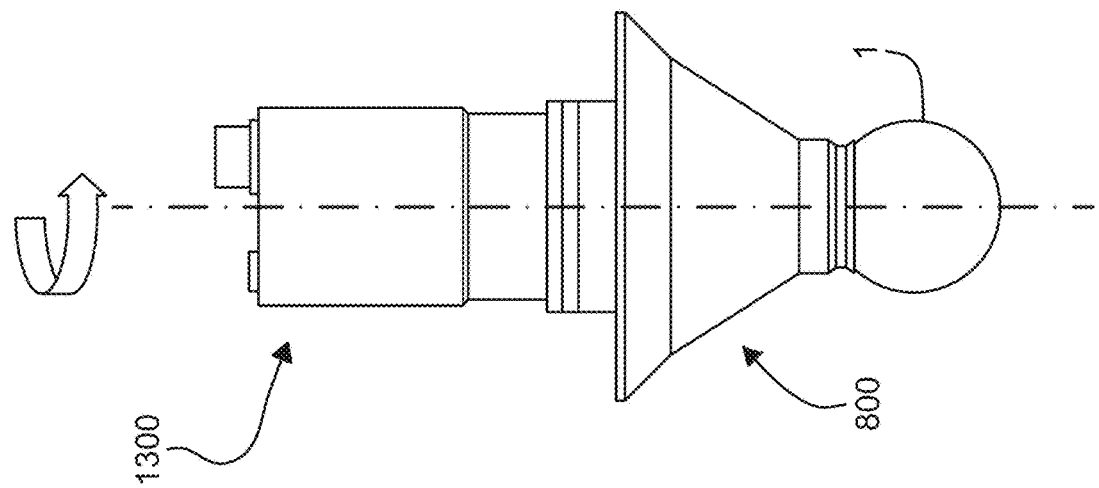
FIGS. 22a and 22b are schematic illustrations of the alignment and diagnostic device together and patient interface being slid and tilted (FIG. 22a) and rotated (FIG. 22b) relative to the eye.
Figure 22A:
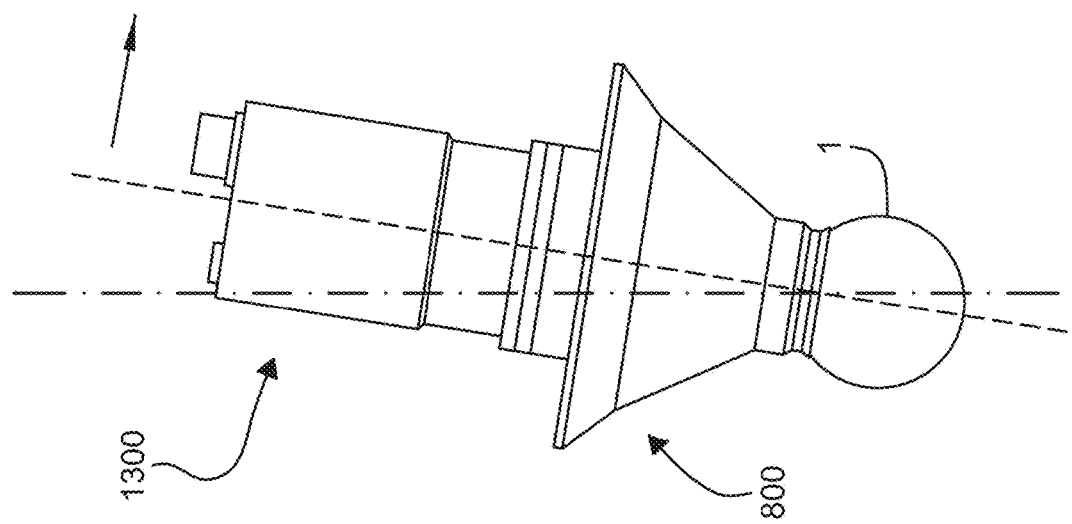

At block 2114 and with reference to FIGS. 19c and 22a, while continuing to observe the image 1900 of the irido-corneal angle 13 captured by the alignment and diagnostic device 1300, the combination of the alignment and diagnostic device and the patient interface 800, is further moved relative to the eye 1 as needed to bring the image of the target surgical location 1909 of the trabecular meshwork 1910 into a substantially central alignment and generally parallel alignment within the surgical overlay mark 1902 and thus substantially within the FSA overlay 1903. As mention above, the FSA overlay 1903 displayed by the alignment and diagnostic device 1300 coincides with the fine surgical area of the surgical laser of the integrated surgical system 1000. As such, orienting the alignment and diagnostic device 1300 so that the target surgical location 1909 is in the FSA overlay 1903 assures that the target volume of ocular tissue is in the FSA of the surgical laser.

At optional block 2116, in cases where the focus of the surgical laser of the integrated surgical system 1000 has a limited depth range, an additional component of the alignment and diagnostic device 1300 may be used to bring one or more depth fiducials of the target surgical location 1909 within the depth range of the laser. For example, a dual aiming beam apparatus 1332 may be used to detect a depth fiducial, such as the surface of the trabecular meshwork 1910 facing the anterior chamber, as disclosed in U.S. patent application Ser. No. 16/781,770, titled "System and Method for Locating a Surface of Ocular Tissue for Glaucoma Surgery Based on Dual Aiming Beams." The dual aiming beams of the apparatus form a single spot on the when the surface of the trabecular meshwork 1910 facing the anterior chamber. The single spot is captured by the camera 1308 and presented on the display 1328 of the alignment and diagnostic device 1300. The single spot may be observed and the alignment and diagnostic device 1300 together with the patient interface 800 may be slid and rotated relative to the eye to place the single spot, and thus the depth fiducial, i.e., the surface of the trabecular meshwork 1910 facing the anterior chamber, within the surgical overlay mark 1902.

In another example, an OCT imaging apparatus 300 may be used to locate a depth fiducial, such as a surface of the trabecular meshwork 1910 facing the Schlemm's canal 1702, or a wall of the Schlemm's canal. With reference to FIGS. 17*a* and 17*b*, one or both of a circumferential OCT scan image 1700 and an azimuthal OCT scan image 1706 of a portion of the irido-corneal angle 13 of the eye may be captured by the OCT imaging apparatus 300 using one or more OCT components 1330 of the alignment and diagnostic device 1300 and displayed together with a surgical overlay mark 1705, 1707. In this case, the images 1700, 1706 may include the Schlemm's canal 1702, the trabecular meshwork 1704, collector channel and blood vessels. These images 1700, 1706 may be observed and the alignment and diagnostic device 1300 together with the patient interface 800 may be moved relative to the eye to place the depth fiducial of interest, e.g., a surface of the trabecular meshwork 1910 facing the Schlemm's canal 1702, or a wall of the Schlemm's canal, within a surgical overlay mark 1705, 1707.

In yet another example, a second harmonic light detection apparatus 1334 may be used to detect a depth fiducial, such as a surface of the trabecular meshwork 1910 facing the Schlemm's canal 1702, or a wall of the Schlemm's canal, as disclosed in as disclosed in U.S. patent application Ser. No. 16/723,883, titled "System and Method for Locating a Structure of Ocular Tissue for Glaucoma Surgery Based on Second Harmonic Light." The second harmonic light may be displayed on the display 1328 of the camera 1308, or a display remote from the alignment and diagnostic device 1300, and may be used to locate the depth fiducial of interest. The second harmonic light may be observed and the alignment and diagnostic device 1300 together with the patient interface 800 may be slid and rotated relative to the eye to place the second harmonic light, and thus the depth fiducial of interest, e.g., a surface of the trabecular meshwork 1910 facing the Schlemm's canal 1702, or a wall of the Schlemm's canal, within the surgical overlay mark 1902.

At block 2118, once the target surgical location 1909 is brought into central alignment with the surgical overlay mark 1902, and optionally at an acceptable depth range, the patient interface 800 is secured to the eye 1. For example, an immobilization device 804 may be activated to secure the patient interface 800 to the eye 1.

At block 2120, the circumferential angular position of the target surgical location 1909 is read and recorded. For example, with reference to FIG. 18*a*, the circumferential angular position may be read from the rotational registration 1802 of the alignment and diagnostic device 1300 that includes a several alignment marks 1804 spaced apart around the circumference of the housing 1806 of the optics structure 1302. This circumferential angular position is subsequently used to align the focusing objective 700 of the surgical system 1000 during laser treatment.

At this point, the process may proceed directly to block 2122. Alternatively, at block 2121 and with reference to FIG. 22*b*, the surgeon may inspect the corneal angle by rotating the alignment and diagnostic device 1300 in the patient interface 800 with respect to the axis of the eye 1 as shown in FIG. 22*b*. In cases where the alignment and diagnostic device 1300 is locked to the patient interface 800, the device is unlocked from the patient interface prior to rotating. The patient interface 800 is locked in place on the eye 1 and does not rotate during maneuver of the alignment and diagnostic device 1300. After the inspection, the process proceeds to block 2122.

At block 2122 and with reference to FIG. 18*a*, the alignment and diagnostic device 1300 is removed from the patient interface 800, while making sure that the patient interface 800 remains attached to the eye 1 and immobilized.

Figure 20B:
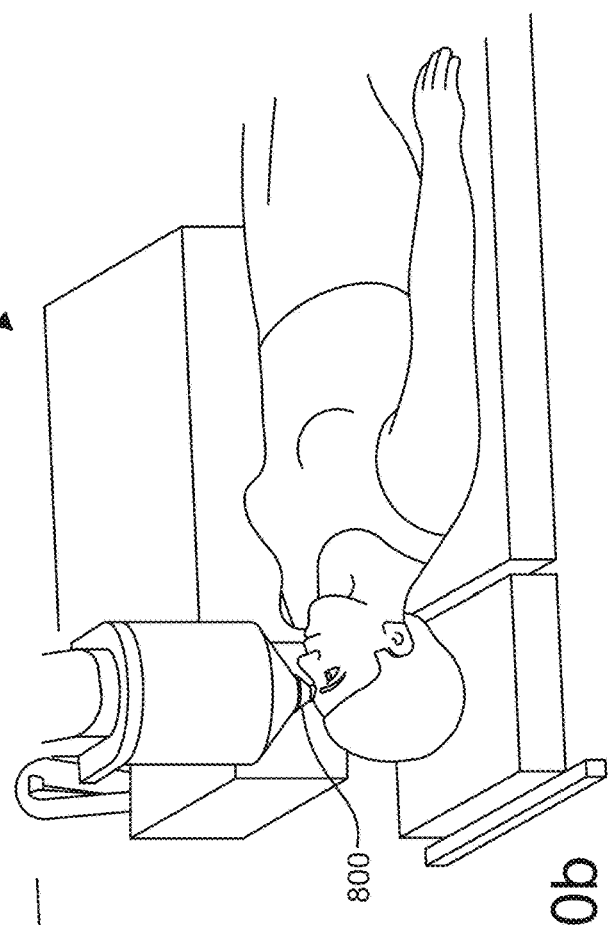
FIGS. 20a and 20b are illustrations of a patient positioned on a surgical bed in proximity with an attachment arm of an integrated surgical system.
Figure 20A:
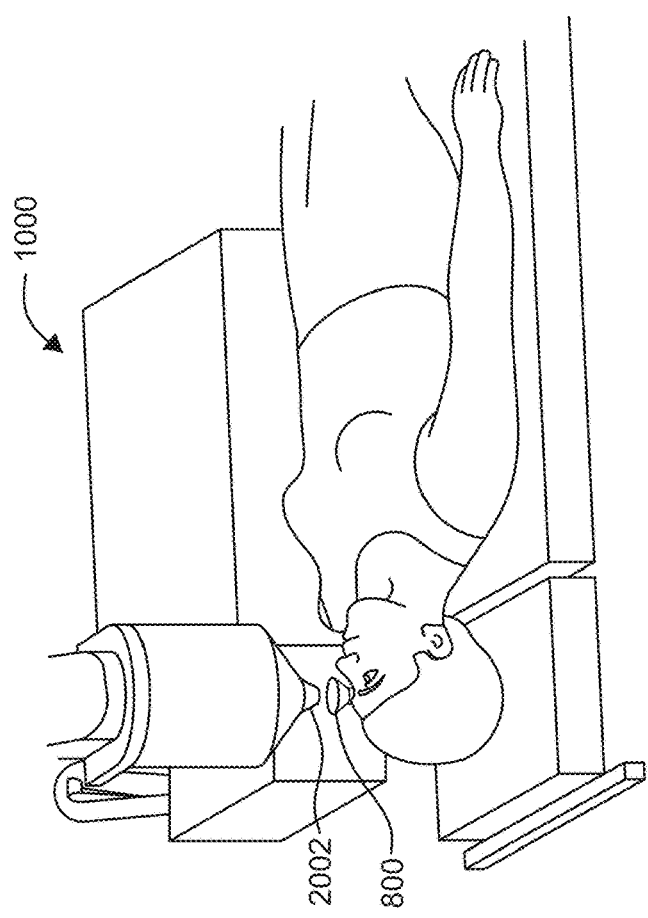

At block 2124 and with reference to FIG. 20*a*, the integrated surgical system 1000 is coupled to the patient interface 800. To this end, the patient interface 800 and the attachment end 2002 of the integrated surgical system 1000 are brought to proximity by moving the surgical bed or the surgical instrument. The attachment end 2002 of the integrated surgical system 1000 includes the focusing objective 700 of the integrated surgical system 1000. With reference to FIG. 20*b*, the attachment end 2002 of the surgical instrument is docked into the patient interface 800 to thereby place the focusing objective 700 into the patient interface. Once the attachment end 2002 of the surgical instrument is docked into the patient interface 800, the patient interface is secured to the focusing objective 700 of the surgical instrument. The patient interface 800 may be secured by engaging the attachment interface 806 of the patient interface.

At block 2126, the circumferential angular position of the surgical aiming of the integrated surgical system 1000 is brought to the circumferential angular position read at block 2120 from the alignment and diagnostic device 1300. An image captured by an imaging device, e.g., the OCT imaging apparatus 300 or the visual microscope 400, of the integrated surgical system 1000 is displayed and observed. The target surgical location 1909 should be observable in the image. The image should correspond to the image shown is FIG. 19*a*, with the target surgical location 1909 being in substantially central alignment within the surgical overlay mark 1902.

At block 2128, the focus of the surgical laser beam is located relative to the target surgical location 1909. For example, the focus may be located at a depth fiducial corresponding to a surface of the trabecular meshwork 1910 facing the anterior chamber, as disclosed in U.S. patent application Ser. No. 16/781,770, titled "System and Method for Locating a Surface of Ocular Tissue for Glaucoma Surgery Based on Dual Aiming Beams." A focus may be placed at a depth fiducial corresponding to a surface of the trabecular meshwork 1910 facing the Schlemm's canal 1702, or a wall of the Schlemm's canal, using one or more OCT images, or as disclosed in as disclosed in U.S. patent application Ser. No. 16/723,883, titled "System and Method for Locating a Structure of Ocular Tissue for Glaucoma Surgery Based on Second Harmonic Light."

At block 2130, optical energy is applied to a target volume of ocular tissue at the target surgical location 1909 in accordance with a treatment pattern. For example, optical energy may be delivered by scanning a laser through a three-dimensional treatment patter to treat glaucoma, as disclosed in U.S. patent application Ser. No. 16/838,858, titled "Method, System, and Apparatus for Generating Three-Dimensional Treatment Patterns for Laser Surgery Of Glaucoma," the disclosure of which is incorporated by reference.

At block 2132, upon completion of laser treatment at the target surgical location 1909, the integrated surgical system 1000 is decoupled from the eye 1 and the patient interface is decoupled from the surgical system. To this end, the immobilization device 804 of the patient interface 800 is disengaged to allow movement of the interface relative to the eye 1. The attachment end 2002 of the integrated surgical system 1000 is then removed from the proximity of the eye 1, together with the patient interface 800. The attachment end 2002 of the integrated surgical system 1000 is then removed from the patient interface 800.

At block 2134, if needed, the process returns to block 2106 and is repeated for an additional target surgical location.

It is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A device for visualizing an irido-corneal angle of an eye through a window of a patient interface configured to be placed on the eye, the device comprising:
    an optics structure configured to engage with the patient interface to provide a line of sight through the window in a direction of the irido-corneal angle, and to subsequently disengage from the patient interface;
    at least one imaging apparatus associated with the optics structure and aligned with the line of sight to enable capturing an image of the eye including the irido-corneal angle; and
    a locking mechanism associated with the optics structure and configured to enable fixation of the optics structure relative to the patient interface at various angular positions around a circumferential extent of the irido-corneal angle, wherein the locking mechanism comprises one or more of:
        a vacuum port coupled to a vacuum source that establishes a vacuum between surfaces of the optics structure and the patient interface,
        a mechanical structure configured to engage a complimentary mechanical structure of the patient interface,
        a magnetic structure coupled to a magnetic source that establishes a magnetic force between the magnetic structure and a magnetic structure of the patient interface, and
        a pneumatic element coupled to a pneumatic source, wherein the pneumatic element is configured to expand against a surface of the patient interface.

2. The device of claim 1, wherein the optics structure is configured to provide the line of sight in the direction of the irido-corneal angle around at least a portion of a circumferential extent of the irido-corneal angle.

3. The device of claim 1, wherein the optics structure is configured to provide the line of sight in the direction of the irido-corneal angle around an entire circumferential extent of the irido-corneal angle.

4. The device of claim 1, wherein the optics structure is configured to rotate relative to the patient interface to enable a capturing of images at various angular positions around a circumferential extent of the irido-corneal angle.

5. The device of claim 1, further comprising a mechanism for providing a measure of a relative angular position between the optics structure and the patient interface.

6. The device of claim 5, wherein the mechanism comprises a rotational registration configured to interface with a corresponding registration on the patient interface.

7. The device of claim 6, wherein the rotational registration is provided by one or more alignment marks associated with at least one of the optics structure and the imaging apparatus.

8. The device of claim 1, wherein the at least one imaging apparatus is configured to couple to the optics structure and the optics structure is configured to rotate relative to the patient interface together with the at least one imaging apparatus.

9. The device of claim 8, wherein the patient interface comprises a wall around the window that defines an interior space and the optics structure is configured to mate within the interior space.

10. The device of claim 9, wherein the interior space of the patient interface is characterized by an interior shape and the optics structure is characterized by an exterior shape similar to the interior shape.

11. The device of claim 9, wherein the optics structure is characterized by an exterior surface that enables rotation of the optics structure relative to the patient interface about a symmetry axis extending through the optics structure and the patient interface.

12. The device of claim 1, wherein the at least one imaging apparatus is a camera.

13. The device of claim 12, wherein the camera comprises one or more of a focusing optics and a magnifier configured to focus and magnify the image captured by the camera.

14. The device of claim 12, wherein the camera further comprises a display for displaying an image captured by the camera.

15. The device of claim 12, wherein the camera further comprises an illumination source configured to output light in the direction of the line of sight into the irido-corneal angle.

16. The device of claim 1, wherein the at least one imaging apparatus comprises one or more optical coherence tomography (OCT) components configured to couple with an OCT apparatus remote from the device.

17. The device of claim 16, wherein the one or more OCT components comprises an OCT scanner head and an interface configured to couple the OCT scanner head to the OCT apparatus.

18. The device of claim 1, wherein the at least one imaging apparatus comprises a dual aiming beam apparatus configured to transmit a first beam of light and a second beam light in the direction of the line of sight into the irido-corneal angle.

19. The device of claim 1, wherein the at least one imaging apparatus comprises a first fiber optic cable having an output aligned in the direction of the line of sight and a second fiber optic cable having an output aligned in the direction of the line of sight, wherein the first and second fiber optic cables are configured to couple to a dual aiming beam apparatus remote from the device so that the first fiber optic cable receives a first beam of light and the second fiber optic cable receives a second beam light.

20. The device of claim 1, wherein the at least one imaging apparatus comprises a second harmonic light detector aligned with the line of sight and configured to determine a location of a focus of a laser beam based on changes in an intensity of a spot of second harmonic light generated by an encounter between the focus and tissue.

21. The device of claim 1, further comprising an interface configured to couple to a laser source and to transmit a laser beam output by the laser source in the direction of the line of sight.

22. A method of aligning an eye for laser treatment of a target volume of ocular tissue in an irido-corneal angle by a laser surgical instrument having a surgical range, the method comprising:
    presenting an image of the eye on a display, wherein:
        the image is captured by an alignment and diagnostic device that is engaged with a patient interface to provide a line of sight in a direction of the irido-corneal angle,
        the display includes a surgical area overlay corresponding to the surgical range of the laser surgical instrument, and
        the alignment and diagnostic device is independent of the laser surgical instrument and is configured to engage with and subsequently disengage from the patient interface;
    updating the display of the image during a movement of the patient interface and the alignment and diagnostic device relative to the eye;
    immobilizing the patient interface relative to the eye when the display indicates that the target volume of ocular tissue is within the surgical area overlay; and
    subsequent to immobilizing the patient interface relative to the eye:
        recording a circumferential angular position of the target volume of ocular tissue from a rotational registration of the alignment and diagnostic device; and
        removing the alignment and diagnostic device from the patient interface.

23. The method of claim 22, wherein the surgical area overlay comprises a coarse surgical area overlay and a fine surgical area overlay located within the coarse surgical area overlay.

24. The method of claim 22, wherein the surgical area overlay further comprises a circumference scanning mark, which indicates a length and an orientation of a circumferential optical coherence tomography (OCT) scan of an OCT imaging apparatus associated with the laser surgical instrument.

25. The method of claim 22, wherein the surgical area overlay further comprises a transverse scanning mark that indicates a length and an orientation of a transverse optical coherence tomography (OCT) scan of an OCT imaging apparatus associated with the laser surgical instrument.

26. The method of claim 22, wherein the surgical range of the laser surgical instrument is characterized by dimensions in the circumferential (x), azimuthal (y) and depth (z) directions.

27. The method of claim 22, further comprising presenting a depth fiducial on the display, wherein the depth fiducial overlays the display and represents a depth spot within the target volume of ocular tissue at which laser treatment is to be initiated.

28. The method of claim 22, wherein the patient interface comprises an immobilization device configured to secure the patient interface to the eye and immobilizing the patient interface relative to the eye comprises engaging the immobilization device.

29. The method of claim 22, further comprising, subsequent to removing the alignment and diagnostic device from the patient interface:
    coupling the laser surgical instrument to the patient interface;
    setting a circumferential angular position of the laser surgical instrument to the circumferential angular position recorded for the alignment and diagnostic device; and
    focusing light from a laser at a spot in the target volume of ocular tissue; and
    applying optical energy at the spot in the target volume of ocular tissue.

30. The method of claim 29, further comprising, prior to focusing light from the laser at a spot in the target volume of ocular tissue:
    presenting an image of the eye on a display, wherein:
        the image is captured by a visual microscope optically coupled to the patient interface, and
        the display includes a surgical area overlay corresponding to the surgical range of the laser surgical instrument.

31. The method of claim 22, further comprising:
    prior to immobilizing the patient interface relative to the eye, determining if a depth fiducial of the target volume of ocular tissue is within a depth range of the laser surgical instrument.

32. The method of claim 31, wherein the determining is based on a relative location of spots of light output by a dual aiming beam apparatus and a surface of the target volume of ocular tissue.

33. The method of claim 31, wherein the determining is based on an interaction of second harmonic light output and one or more anatomical landmarks of the target volume of ocular tissue.

* * * * *